US012620456B2

(12) United States Patent
Ren et al.

(10) Patent No.: US 12,620,456 B2
(45) Date of Patent: May 5, 2026

(54) DATA PROCESSING METHOD AND APPARATUS FOR QUANTUM CHEMISTRY SYSTEM

(71) Applicant: Beijing Youzhuju Network Technology Co., Ltd., Beijing (CN)

(72) Inventors: Weiluo Ren, Beijing (CN); Chenlin Chai, Beijing (CN); Weizhong Fu, Beijing (CN); Ji Chen, Beijing (CN)

(73) Assignee: Beijing Youzhuju Network Technology Co., Ltd., Beijing (CN)

( * ) Notice: Subject to any disclaimer, the term of this patent is extended or adjusted under 35 U.S.C. 154(b) by 0 days.

(21) Appl. No.: 18/743,590

(22) Filed: Jun. 14, 2024

(65) Prior Publication Data

US 2025/0174307 A1    May 29, 2025

Related U.S. Application Data

(63) Continuation of application No. PCT/CN2023/088084, filed on Apr. 13, 2023.

(30) Foreign Application Priority Data

Apr. 15, 2022    (CN) .......................... 202210395445.9

(51) Int. Cl.
   *G16C 10/00*        (2019.01)
   *G16C 20/70*        (2019.01)
(52) U.S. Cl.
   CPC ............. *G16C 10/00* (2019.02); *G16C 20/70* (2019.02)

(58) Field of Classification Search
   CPC ................................ G16C 10/00; G16C 20/70
   See application file for complete search history.

(56) References Cited

U.S. PATENT DOCUMENTS

| 2003/0143427 A1 | 7/2003 | Matsuo et al. |
| 2021/0011748 A1 | 1/2021 | Lee et al. |

(Continued)

FOREIGN PATENT DOCUMENTS

| CN | 108287881 A | 7/2018 |
| CN | 108595820 A | 9/2018 |

(Continued)

OTHER PUBLICATIONS

Pfau et al. Ab Initio Solution of The Many-Electron Schrodinger Equation With Deep Neural Networks Physical Review Research 2, 033429 2020 (Year: 2020).*

(Continued)

*Primary Examiner* — Rehana Perveen
*Assistant Examiner* — Cuong V Luu
(74) *Attorney, Agent, or Firm* — Alleman Hall LLP

(57)        ABSTRACT

The present disclosure relates to a data processing method and apparatus for a quantum chemistry system. The data processing method for a quantum chemistry system comprises the following steps: acquiring a specific wave function which is constructed on the basis of a neural network and is suitable for a quantum chemistry system; performing walker processing on the basis of the specific wave function, the walker processing comprising diffusion processing of walkers; and determining related information about chemical properties of the quantum chemistry system on the basis of the specific wave function and the processed walkers.

20 Claims, 9 Drawing Sheets

(56) References Cited

U.S. PATENT DOCUMENTS

| | | | |
|---|---|---|---|
| 2021/0117776 A1 | 4/2021 | Cheng et al. |
| 2021/0365606 A1 | 11/2021 | Yu et al. |

FOREIGN PATENT DOCUMENTS

| | | |
|---|---|---|
| CN | 111126611 A | 5/2020 |
| CN | 113710609 A | 11/2021 |
| CN | 113723584 A | 11/2021 |
| CN | 114758733 A | 7/2022 |
| WO | 2021211470 A1 | 10/2021 |

OTHER PUBLICATIONS

Dearnbach et al. Quantum Walk Neural Networks With feature Dependent Coins Applied Network Science, 2019 (Year: 2019).*

China National Intellectual Property Administration, Office Action and Search Report Issued in Application No. 202210395445.9, May 17, 2024, 13 pages.

Hermann, J. et al., "Deep-neural-network solution of the electronic Schrodinger equation," Nature Chemistry, vol. 12, Sep. 23, 2020, 11 pages.

Huang, H. et al., "Study of Trial Wave Function for Fixed-Node Quantum Monte Carlo Method," Chemical Research and Application, vol. 8, No. 3, 1996, 4 pages. Contains English abstract on final page.

ISA China National Intellectual Property Administration, International Search Report and Written Opinion Issued in Application No. PCT/CN2023/088084, Jun. 23, 2023, WIPO, 5 pages.

Needs, R.J. et al., "Variational and diffusion quantum Monte Carlo calculations with the Casino code," The Journal of Chemical Physics, vol. 152, No. 15, Apr. 21, 2020, 42 pages.

Pfau, D. et al., "Ab initio solution of the many-electron Schrödinger equation with deep neural networks," Physical Review Research, vol. 2, No. 3, Sep. 16, 2020, 15 pages.

Yang, M. et al., "Improved walker population control for full configuration interaction quantum Monte Carlo," The Journal of Chemical Physics, vol. 153, No. 17, Nov. 7, 2020, 15 pages.

European Patent Office, Extended European Search Report Issued in Application No. 23787795.6, Mar. 10, 2025, Germany, 11 pages.

Wilson, M. et al., "Simulations of state-of-the-art fermionic neural network wave functions with diffusion Monte Carlo," arXiv:2103.12570v2, Mar. 24, 2021, 20 pages.

Esler, K. et al., "Accelerating Quantum Monte Carlo Simulations of Real Materials on GPU Clusters," Computing in Science & Engineering, vol. 14, No. 1, Oct. 14, 2010, 12 pages.

Mcfarland, J. et al., "Gradient Descent Optimization of Fermion Nodes in Diffusion Monte Carlo," arXiv:2112.14182v2, Mar. 3, 2022, 11 pages.

Inack, E. M. et al., "Projective quantum Monte Carlo simulations guided by unrestricted neural network states," arXiv:1809.03562v1, Sep. 10, 2018, 10 pages.

European Patent Office, Office Action Issued in Application No. 23787795.6, Oct. 24, 2025, Germany, 9 pages.

Assaraf, R. et al., "Diffusion Monte Carlo methods with a fixed number of walkers," Physical Review E, vol. 61, No. 4, Apr. 1, 2000, 10 pages.

* cited by examiner

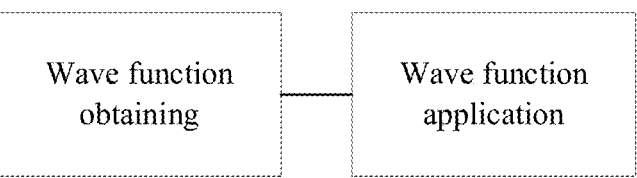

Acquire a specific wave function suitable for a quantum chemical system that is constructed based on a neural network

S202

Perform walker processing based on the specific wave function, the walker processing including diffusion of walkers

S203

Determine related information about chemical properties of the quantum chemical system based on the specific wave function and the processed walkers

FIG. 2A

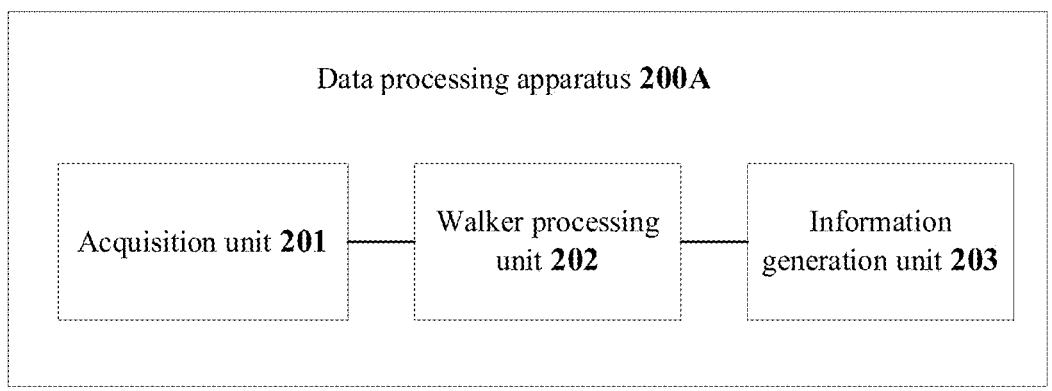

Data processing apparatus 200A

Acquisition unit 201 — Walker processing unit 202 — Information generation unit 203

FIG. 2D

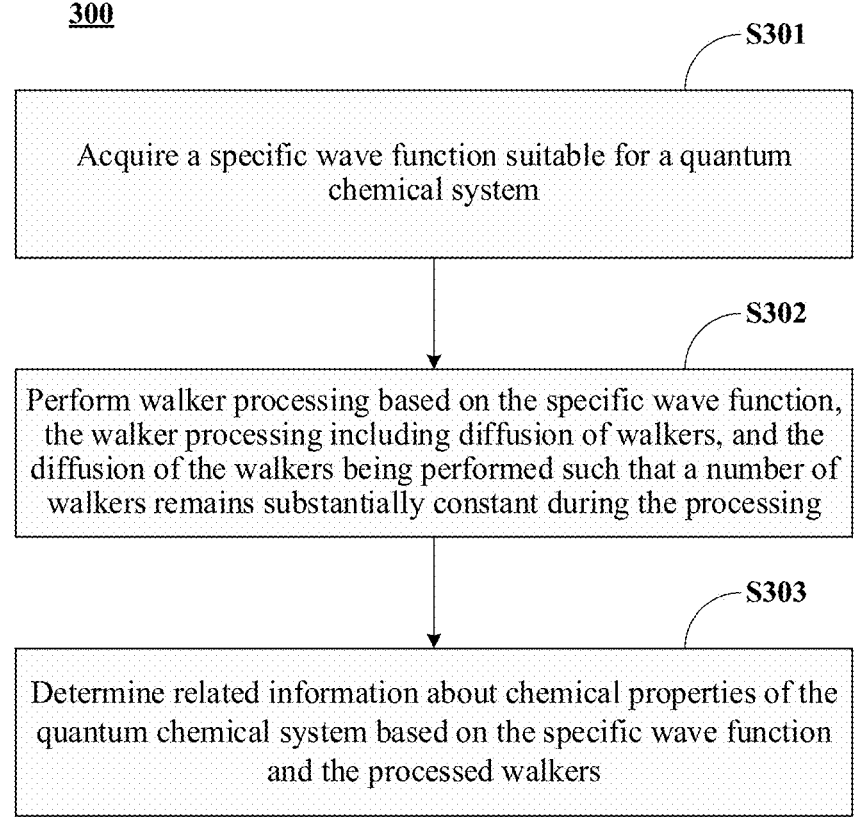

300

S301

Acquire a specific wave function suitable for a quantum chemical system

S302

Perform walker processing based on the specific wave function, the walker processing including diffusion of walkers, and the diffusion of the walkers being performed such that a number of walkers remains substantially constant during the processing

S303

Determine related information about chemical properties of the quantum chemical system based on the specific wave function and the processed walkers

FIG. 3A

DATA PROCESSING METHOD AND APPARATUS FOR QUANTUM CHEMISTRY SYSTEM

CROSS-REFERENCE TO RELATED APPLICATIONS

The present application is a continuation application of PCT/CN2023/088084 filed Apr. 13, 2023, which is based on and claims priority to Chinese Application No. 202210395445.9, filed on Apr. 15, 2022, both the above-mentioned applications are incorporated herein by reference in their entireties.

TECHNICAL FIELD

The present disclosure relates to the field of quantum chemistry, and in particular, to data processing for a chemical system.

BACKGROUND ART

Quantum chemistry is an important branch of theoretical chemistry. Its research scope may include structures and properties of stable and unstable molecules, and relationships between the structures and properties; interaction between molecules; and mutual collisions and reactions between molecules, and other issues. The main theoretical basis in the quantum chemistry research is quantum mechanics, which describes the laws that govern operations in the microscopic world.

SUMMARY OF THE INVENTION

The Summary is provided to give a brief overview of concepts, which will be described in detail later in the section Detailed Description of Embodiments. The Summary is neither intended to identify key or necessary features of the claimed technical solutions, nor is it intended to be used to limit the scope of the claimed technical solutions.

In a first aspect of the present disclosure, there is provided a data processing method for a quantum chemical system, the method may include the following steps: acquiring a specific wave function suitable for the quantum chemical system that is constructed based on a neural network; performing walker processing based on the specific wave function, the walker processing including diffusion of walkers; and determining related information about chemical properties of the quantum chemical system based on the specific wave function and the processed walkers.

In a second aspect of the present disclosure, there is provided a data processing apparatus for a quantum chemical system. The apparatus may include: an acquisition unit configured to acquire a specific wave function suitable for the quantum chemical system that is constructed based on a neural network; a walker processing unit configured to perform walker processing based on the specific wave function, the walker processing including diffusion of walkers; and an information generation unit configured to determine related information about chemical properties of the quantum chemical system based on the specific wave function and the processed walkers.

In a third aspect of the present disclosure, there is provided a data processing method for a quantum chemical system, the method may include the following steps: acquiring a specific wave function suitable for the quantum chemical system; performing walker processing based on the specific wave function, the walker processing including diffusion of walkers, and the diffusion of the walkers being performed such that the number of walkers remains constant during the processing; and determining related information about chemical properties of the quantum chemical system based on the specific wave function and the processed walkers.

In a fourth aspect of the present disclosure, there is provided a data processing apparatus for a quantum chemical system, the apparatus may include an acquisition unit configured to acquire a specific wave function suitable for the quantum chemical system; a walker processing unit configured to performs walker processing based on the specific wave function, the walker processing including diffusion of walkers, and the diffusion of the walkers being performed such that the number of walkers remains constant during the processing; and an information generation unit that determines related information about chemical properties of the quantum chemical system based on the specific wave function and the processed walkers.

In a fifth aspect of the present disclosure, there is provided an electronic device. The electronic device includes: a memory storing instructions; and a processor, wherein the instructions, when executed by the processor, cause the method according to any one of the embodiments of the present disclosure to be implemented.

In a sixth aspect of the present disclosure, there is provided a computer-readable storage medium having a computer program stored thereon, wherein the program, when executed by a processor, causes the method according to any one of the embodiments of the present disclosure to be implemented.

In a seventh aspect of the present disclosure, there is provided a computer program product including instructions that, when executed by a processor, cause the method according to any one of the embodiments of the present disclosure to be implemented.

In an eighth aspect of the present disclosure, there is provided a computer program including program codes that, when executed by a processor, cause the method according to any one of the embodiments of the present disclosure to be implemented.

Through the following detailed description of exemplary embodiments of the present disclosure with reference to the drawings, other features, aspects, and advantages of the present disclosure will become clear.

BRIEF DESCRIPTION OF DRAWINGS

Preferred embodiments of the present disclosure are described below with reference to the drawings. The drawings illustrated here are used to provide a further understanding of the present disclosure, and together with the following detailed description, are incorporated in and form a part of the specification, to explain the present disclosure. It should be understood that the drawings in the following description relate to only some embodiments of the present disclosure, and do not constitute a limitation on the present disclosure. In the drawings:

FIG. 1 schematically shows a basic concept of research/analysis of chemical properties of a quantum chemical system according to an embodiment of the present disclosure;

FIG. 2A is a flowchart of a data processing method for a quantum chemical system according to a first embodiment of the present disclosure;

FIG. 2D is a block diagram of a data processing apparatus for a quantum chemical system according to a first embodiment of the present disclosure;

FIG. 3A is a flowchart of a data processing method for a quantum chemical system according to a second embodiment of the present disclosure;

Figure 2B:
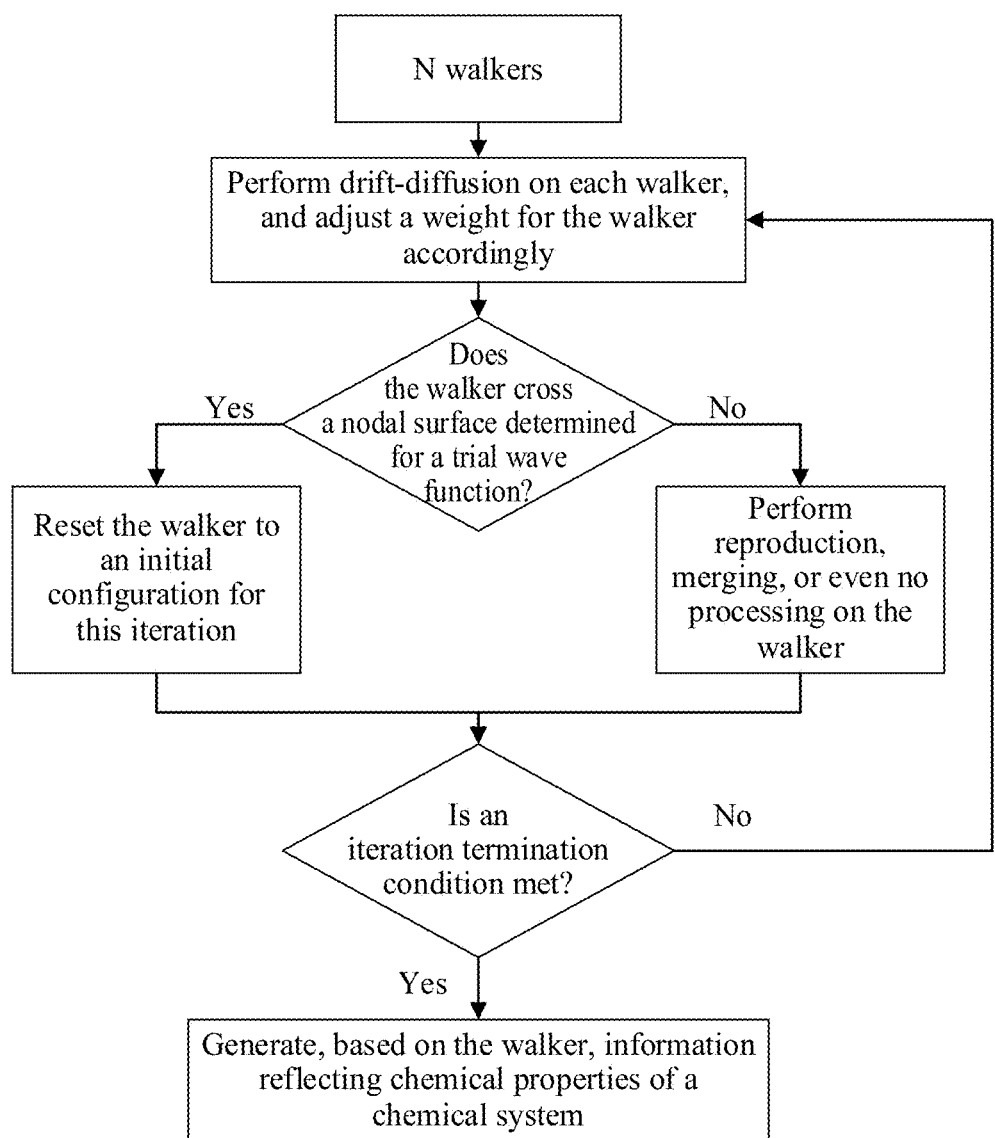
FIG. 2B shows iterative walker processing according to a first embodiment of the present disclosure.

It should be understood that, for ease of description, the sizes of various parts shown in the drawings are not necessarily drawn to actual scale. The same or similar reference numerals in the drawings are used to denote the same or similar components. Therefore, once an item has been defined in one of the drawings, it may not be further discussed in the subsequent drawings.

DETAILED DESCRIPTION OF THE INVENTION

The technical solutions in the embodiments of the present disclosure are clearly and completely described below with reference to the drawings of the embodiments of the present disclosure. However, apparently, the embodiments described are merely some embodiments of the present disclosure rather than all the embodiments. The following description of the embodiments is actually merely illustrative, and in no way serves as any limitation to the present disclosure and application or use thereof. It should be understood that the present disclosure may be implemented in various forms and should not be construed as being limited to the embodiments set forth here.

It should be understood that the various steps described in the method implementations of the present disclosure may be performed in different orders, and/or performed in parallel. Furthermore, additional steps may be included and/or the execution of the illustrated steps may be omitted in the method implementations. The scope of the present disclosure is not limited in this respect. Unless specifically stated otherwise, the relative arrangement of components and steps, numerical expressions, and numerical values set forth in these embodiments should be construed as merely exemplary, and do not limit the scope of the present disclosure.

The term "include" and the variations thereof used in the present disclosure are open-ended terms that include at least subsequent elements/features but do not exclude other elements/features, that is, "including but not limited to". In addition, the term "comprise" and the variations thereof used in the present disclosure are open-ended terms that comprise at least subsequent elements/features but do not exclude other elements/features, that is, "comprising but not limited to". In the context of the present disclosure, "include" has the same meaning as "comprise". The term "based on" means "at least partially based on".

The terms "one embodiment", "some embodiments", or "an embodiment" described throughout the specification means that the specific features, structures, or characteristics described in connection with the embodiments are included in at least one embodiment of the present invention. For example, the term "one embodiment" means "at least one embodiment". The term "another embodiment" means "at least one another embodiment". The term "some embodiments" means "at least some embodiments". Moreover, the phrases "in one embodiment", "in some embodiments", or "in an embodiment" appearing in various places throughout the specification do not necessarily all refer to the same embodiment, but may also refer to the same embodiment. It should be noted that the modifiers "one" and "a plurality of" mentioned in the present disclosure are illustrative and not restrictive, and those skilled in the art should understand that unless the context clearly indicates otherwise, the modifiers should be understood as "one or more".

It should be noted that concepts such as "first" and "second" mentioned in the present disclosure are only used to distinguish different apparatuses, modules, or units, and are not used to limit the sequence of functions performed by these apparatuses, modules, or units or interdependence. Unless otherwise specified, concepts such as "first" and "second" are not intended to imply that the objects described in this way must be in a given order in terms of time, space, or ranking, or in any other given order.

In a chemical research system, quantum chemistry has always attracted great attention, especially in research on a chemical system through the application of quantum mechanics. The research on the chemical system mainly involves research/analysis for acquiring chemical properties of the chemical system, and the chemical properties of the chemical system may include any appropriate properties/attributes, such as attributes/indicators related to energy, and so on. Specifically, ground-state energy of the chemical system is very important for quantum chemistry research, for example, a capability to accurately calculate the ground-state energy helps chemists to develop new materials, such as new materials used to accelerate agricultural nitrogen fixation and a hydrolysis process for making clean energy, and so on.

When analysis/research is performed on the chemical system in quantum chemistry, such as determining chemical properties of the chemical system, various algorithms are usually employed to solve a Schrodinger equation for a microscopic system, so as to approximately obtain the chemical properties/performance of the quantum chemical system. The Schrodinger equation is a basic equation for quantum mechanics, which reveals the basic laws of motion of matter in the microscopic chemical world. In the process of solving approximations, many such algorithms face a key problem, that is, the selection of a wave function approximation. High-accuracy wave functions are very important for obtaining accurate solutions for chemical performance. In addition, in quantum chemistry, the data processing efficiency is also very important for analysis/research of the chemical system, such as determining the chemical properties of the chemical system.

In view of this, the present disclosure provides an improved data processing technique for a quantum chemical system. In an aspect of the present disclosure, a high-accuracy wave function can be constructed, and on basis of application of the wave function, a specific quantum chemical method can be applied to further process data, so that accurate solutions for chemical performance can be obtained. Specifically, the present disclosure proposes the use of a neural network to construct a wave function, and applies the constructed wave function as a trial wave function to a specific quantum chemical method, especially a diffusion Monte Carlo method. This allows for leveraging a strong fitting capability of the neural network to acquire/construct a high-accuracy wave function, thereby improving the accuracy of the specific quantum chemical method, especially the diffusion Monte Carlo method, and thus achieving accurate research/analysis of the chemical system in quantum chemistry.

In another aspect of the present disclosure, a specific processing device can be utilized to perform data processing in the quantum chemical system in an appropriate manner. The specific processing device may be a GPU or another processing resource of an appropriate type. In addition, corresponding to such a specific chemical processing resource, the data processing process can be adaptively optimized, thereby particularly improving data processing effects in the quantum chemical system, especially the data processing efficiency.

In still another aspect of the embodiments of the present disclosure, it is proposed that a wave function can be constructed based on the neural network, and the constructed wave function can be applied as a trial wave function to the specific quantum chemical method, especially the diffusion Monte Carlo method, and during the operation of the specific quantum chemical method (especially the diffusion Monte Carlo method), a specific processing device can be used to perform data processing in the quantum chemical system in an appropriate manner. In this way, improvements can be achieved in both data processing accuracy and processing efficiency.

The embodiments of the present disclosure are described in detail below with reference to the drawings. However, the present disclosure is not limited to these specific embodiments. The following specific embodiments may be combined with each other, and the same or similar concepts or processes may not be repeated in some embodiments. Furthermore, in one or more embodiments, specific features, structures, or characteristics may be combined in any suitable manner that would be clear to those of ordinary skill in the art from the present disclosure.

FIG. 1 is a diagram schematically showing a general concept of research/analysis of chemical properties of a quantum chemical system according to an embodiment of the present disclosure. As a general concept, an appropriate wave function may be acquired in advance, and then the acquired wave function may be applied for processing. Specifically, a wave function that characterizes the quantum chemical system, especially a state of a microscopic system of the quantum chemical system, is acquired, and the acquired wave function is applied to determine chemical properties of the quantum chemical system.

According to embodiments of the present disclosure, the chemical properties of the quantum chemical system are particularly attributes related to ground-state energy. In quantum chemistry, the energy of a chemical system can only have some specific values. The lowest energy is called ground-state energy, a corresponding state of the system is called a ground state, and its corresponding wave function is called a ground-state wave function. The other states are all called excited states. In embodiments of the present disclosure, the attributes related to the ground-state energy may be represented in various appropriate forms, especially in relative values of the ground-state energy. For example, when the ground-state energy and several excited-state energies can be obtained, attributes related to the ground-state energy may be represented as ratios of the ground-state energy to other excited-state energies, etc.

In embodiments of the present disclosure, the wave function acquired in advance may be used as a trial wave function, which may serve as a basis for subsequent analysis/research of the quantum chemical system, such as determining the chemical properties of the quantum chemical system. Specifically, the wave function acquired in advance may particularly serve as a trial wave function for the diffusion Monte Carlo method. The wave function may be any appropriate wave function, in some embodiments of the present disclosure, the wave function is a function that describes states of a microscopic system, particularly a wave function that describes electronic states. An input of the wave function may be information about a state/attribute of an electron, for example, a spatial coordinate of the electron, and a square modulus of an output of the wave function is proportional to a probability of the electron appearing at this location.

According to embodiments of the present disclosure, a quantum chemical method/process applying the wave function may include performing walker simulation based on the wave function, thereby simulating/determining the chemical properties of the quantum chemical system by calculating related statistics of walkers. In some embodiments, such a quantum chemical method/process may particularly be the diffusion Monte Carlo method, and the wave function constructed according to the embodiments of the present disclosure may be applied as a trial wave function to the diffusion Monte Carlo method.

In embodiments of the present disclosure, statistical characteristics of the processed walkers may characterize the chemical properties of the chemical system that are desired/required to be acquired, such as attributes of specific energy. As an example, a walker may include information about attributes of electrons in the chemical system, particularly information related to a distribution of the electrons. For example, in the diffusion Monte Carlo method, the walkers used may include two parts: position coordinates of all electrons in the system and their corresponding weights.

The embodiments according to the present disclosure will be mainly described below with reference to the ground-state energy in the quantum chemical system. In the present disclosure, the ground state means a state that the energy of the chemical system in quantum chemistry is lowest, and the ground-state energy refers to a lowest energy state of a molecule. However, it should be noted that the ground-state energy is merely exemplary and not restrictive. Depending on the application scenarios and application requirements, the embodiments according to the present disclosure may also be applied to research/analysis of other chemical attitudes/energies of the quantum chemical system, for example, any required energy, such as any required excited-state energy, and in this case, adaptive adjustments can be made on the basis of the solutions of the present disclosure with respect to requirements.

FIG. 2A is a flowchart of a data processing method for a quantum chemical system according to an embodiment of the present disclosure. In the context of the present disclosure, data processing for the quantum chemical system is specifically data processing related to chemical attributes of the quantum chemical system, which may, for example, include, but not limited to, computing, fitting, etc. of data/numeric values/information, etc. The chemical system in quantum chemistry as mentioned in the present disclosure (hereinafter referred to as a quantum chemical system or chemical system) refers to a molecule formed by some single atoms or multiple atoms in specific configurations, and a microscopic image of the molecule may include an atomic nucleus located at a relatively fixed position and electrons moving freely therein. The embodiments according to the present disclosure are particularly suitable for molecular-scale applications.

In the method 200, in step S201, a specific wave function suitable for the quantum chemical system that is constructed based on a neural network is acquired. In step S202, walker processing is performed based on the specific wave function, the walker processing including diffusion of walkers. In step S203, related information about chemical properties of the quantum chemical system is determined based on the specific wave function and the processed walkers.

According to embodiments of the present disclosure, the specific wave function may be a function that describes a state of a microscopic system of the chemical system. In some embodiments of the present disclosure, an input of the wave function may be information about parameters in the state of the microscopic system of the quantum chemical system, and an output of the wave function may be a property characterizing the quantum chemical system. In some embodiments, the information about parameters in the state of the microscopic system may mean, for example, information related to states/properties of electrons in the chemical system, including but not limited to information related to a spatial distribution of electrons in a solid system. The information related to spatial distribution of electrons may include or be based on spatial coordinates of all electrons (such as three-dimensional spatial coordinates, which may be in a vector form), etc. The properties of the quantum chemical system may include energy-related states, distribution-related states, etc. Generally, in the quantum chemical system, the atomic nucleus located at a relatively fixed position serves as a skeleton, while the electrons move freely relative to the nucleus. Therefore, in one embodiment, the specific wave function is a wave function that characterizes electronic states in the chemical system. An input of the wave function may be information about a state/attribute of the electron, for example, spatial coordinates of all electrons in the system, and a square modulus of an output of the wave function is proportional to a probability of the electron appearing at this location.

In embodiments of the present disclosure, the trial wave function is an auxiliary wave function used to reduce energy variance and fix a nodal surface during data processing. Generally, the accuracy of research/analysis of the chemical properties of the quantum chemical system is limited by the nodal surface of the trial wave function. The closer the nodal surface of the trial wave function is to a nodal surface of a true ground-state wave function, the closer energy obtained by walker processing based on the trial wave function is to true ground-state energy. The present disclosure proposes to use a neural network to construct the wave function, and apply the constructed wave function as the trial wave function to a specific quantum chemical method, particularly a diffusion Monte Carlo method, which allows for leveraging a strong fitting capability of the neural network to acquire/construct a high-accuracy wave function, thereby improving the accuracy of the specific quantum chemical method, especially the accuracy of the diffusion Monte Carlo method, and thus achieving accurate research/analysis of the chemical system in quantum chemistry. According to embodiments of the present disclosure, the specific wave function constructed based on the neural network may serve as a basis for subsequent processing of walkers, and the closer the nodal surface of the trial wave function is to the nodal surface of the true ground-state wave function, the closer the energy obtained by the walker processing based on the trial wave function is to the true ground-state energy. Therefore, a more accurate result can be obtained, for example, a more accurate ground-state wave function and ground-state energy can be obtained.

In some embodiments of the present disclosure, the wave function may be determined/trained in various appropriate manners, and may specifically be computed by using a corresponding model (for example, a neural network model). Specifically, during training, the input is an initial electron configuration (for example, spatial coordinates of all the electrons), and then the neural network model may output a wave function for any configuration. The network is trained to find an approximation of the ground-state wave function by minimizing the energy state. Specifically, during training, the network modifies its parameters until the energy reaches a minimum value, with corresponding network parameters corresponding to the ground-state wave function.

According to embodiments of the present disclosure, a neural network may be trained first, and after completion of the training, parameters of the neural network may be fixed, that is, a wave function characterized by the neural network may be fixed, then the wave function can be used as a trial wave function to carry out the walker simulation according to the present disclosure to obtain a more accurate ground-state wave function and ground-state energy. In some embodiments, the neural network may be trained in various appropriate manners. For example, it may be trained using various wave function construction methods known in the art. Preferably, the specific wave function is obtained by training the neural network using a variational Monte Carlo method. In some embodiments, various appropriate neural networks may be used to construct the specific wave function according to embodiments of the present disclosure as the trial wave function. In some embodiments, a "Fermi neural network" may be used to construct the trial wave function according to embodiments of the present disclosure. Specifically, the Fermi neural network is trained first using the variational Monte Carlo method, and after completion of the training, parameters of the neural network are fixed, that is, a wave function characterized by the neural network is fixed. In some embodiments, another neural network method in quantum chemistry, such as a "Pauli neural network" or the like, may alternatively be used.

According to embodiments of the present disclosure, the walkers may be parameters used in quantum chemical computations, and may mean sample points for sampling. As an example, the walkers may indicate sampling points for sampling with respect to a given distribution (e.g., a distribution acquired using a trial basis function). In some embodiments, the walkers may correspond to electrons in the microscopic system of the quantum chemical system, such as the information about electron attributes as described above that includes the spatial coordinates of electrons and the corresponding weights. According to embodiments of the present disclosure, after proper processing of the walkers, statistical information about the walkers may indicate specific energy in the microscopic system of the quantum chemical system, especially the ground-state energy.

According to embodiments of the present disclosure, a walker may be expressed in various appropriate forms. As an example, the walker may be in the form of a vector, where dimensions of the vector may depend on the number of electrons in the chemical system, such as the product of the number of electrons and the number of spatial dimensions (e.g., the number is 3, for a three-dimensional space). Furthermore, in some embodiments, the walker may be initially set in any appropriate manner, and specifically, the walker is initially set randomly. As an example, considering that a specific molecule, such as a water molecule, has 10 electrons therein, one walker may correspond to coordinates of 10 electrons in the three-dimensional space, and thus the walker is a 30-dimensional vector. However, in the initial setting, values in the vectors of walker may be randomly set, for example, numerical values in the 30-dimensional vector may be random.

According to embodiments of the present disclosure, data processing of walkers can be performed based on the trial wave function. Specifically, walker simulation/processing can be performed based on the improved wave function constructed using the neural network, to accurately acquire chemical performance. In some embodiments, the walker processing may include diffusion. Specifically, during the diffusion, the walker may be diffused with drift and a weight for the walker can be adjusted accordingly. According to embodiments of the present disclosure, the adjustment of the weight for the walker during the diffusion may be performed in any appropriate manner in the art, for example, the adjustment may particularly be performed based on energy of the diffused walker.

In some embodiments, the walker processing may further include performing a detection on such diffusion, especially on the diffused walkers, based on the trial wave function, preferably performing a crossing detection based on the nodal surface of the trial wave function, and performing corresponding processing based on a detection result. According to embodiments of the present disclosure, the nodal surface of the wave function is all of points of the function that have a value of zero. According to this embodiment of the present disclosure, based on the nodal surface of the trial wave function, the nodal surface crossing detection is performed on the diffused walkers, that is, it is judged whether the diffused walkers cross the nodal surface of the wave function, and appropriate processing is performed on the diffused walkers based on a judgement result. The processing may specifically involve configuration, such as position, quantity, or weight, of the walkers. Such processing may be considered to be included in the diffusion, or may certainly be performed after the diffusion. According to embodiments of the present disclosure, whether the walker crosses the nodal surface of the constructed wave function may be judged by determining whether a spatial position of the diffused walker crosses the nodal surface, which may be performed in various appropriate manners in the art and will not be described in detail here.

According to embodiments of the present disclosure, when a walker dose not cross the nodal surface of the constructed wave function, appropriate processing is performed on the walker. Specifically, the appropriate processing may involve adjustment of configuration of the walkers, particularly adjustment of the position, quantity, weight, etc. of the walkers, especially adjustment based on the weights for the walkers. In some embodiments, the processing may be performed based on the weights for the diffused walkers, for example, the processing may include at least one of reproduction, merging, or even no operation. Specifically, if a weight for a walker is too large after adjustment, for example, greater than or equal to a first specific threshold (which may be referred to as a first weight threshold), reproduction is performed. Reproduction may also be referred to as derivation, duplication, etc., and may be performed in various appropriate manners in the art, and may particularly include duplicating a walker whose weight is greater than the first specific threshold, where a weight for each of two walkers obtained through duplication is half of the weight for the original walker. As an example, coordinates of the duplicated walkers may be appropriately set, for example, may especially be located at the original position, which will not be described in detail here. In another aspect, if the weight for the diffused and weight adjusted walker is too small, for example, less than a second specific threshold (which may be referred to as a second weight threshold), merging is performed, specifically, the merging merges two appropriate walkers into a single walker, and the walkers to be merged may be appropriately selected, for example, based on weights, positions of the walkers, or correlation between the walkers. As an example, walkers less than the weight may be merged, or walkers at the same computing node may be merged, and so on. In some embodiments, the attribute (e.g., a weight, spatial coordinates, etc.) of a merged walker may be derived based on attributes of the two walkers being merged, which may be implemented in various appropriate manners in the art, for example, a weight for the merged walker may be a mathematical statistical value of weights for the two walkers being merged, such as the sum of the weights, for example, the coordinate of the merged walker may be the coordinate of one of the two walkers being merged, or may be an appropriate coordinate between the two walkers, such as intermediate coordinate, etc., which will not be described in detail here. In yet another aspect, if the weight for the walker is greater than or equal to the second specific threshold and less than the first specific threshold, there is no need to perform further processing on the walker, that is, the reproduction or merging as described above will not be performed on the diffused walker.

In some embodiments, the above-mentioned processing, especially the reproduction and the merging, may be performed based on specific application requirements, processing configurations, etc., without being only limited to or dependent on weights, for example, the reproduction and the merging may be performed in a correlated manner, which will be described in detail below.

According to embodiments of the present disclosure, when a walker crosses the nodal surface of the constructed wave function, the walker may be reset/reinitialized. Specifically, the attributes of the walker may be restored to the attributes before diffusion, for example, the position and weight of the walker may be restored to its position and weight before diffusion.

According to embodiments of the present disclosure, the diffusion of walkers may be iteratively performed. FIG. 2B is a diagram of a concept of exemplary walker diffusion iteratively performed. Specifically, in each iteration, a walker may be diffused and a weight for the walker may be adjusted, and then a detection may be performed on the diffused walker based on the trial wave function, especially a nodal surface crossing detection may be performed on the diffused walker based on the nodal surface of the trial wave function, and a walker which is detected as crossing the nodal surface is reset, while a walker which is not detected as crossing the nodal surface will be appropriately processed, for example, reproduction, merging, or even no processing will be performed on the walker, then, it is verified whether an iteration termination condition is met after this iteration, and if the termination condition is not met, walker processing continues to be performed, otherwise the chemical properties of the chemical system can be determined based on a processing result of the walkers. It should be noted that, FIG. 2B is merely exemplary, and the processing flow may be appropriately adjusted, for example, it can be first verified whether the iteration termination condition is met, and then when the termination condition is not met, diffusion, weight adjustment, reproduction, merging, or the like of the walker may continue to be performed. Specific processing in the diffusion of walkers will be described in detail below.

In some embodiments, in each iteration of the diffusion of walkers, at least the following operations may be included: performing drift-diffusion and then performing weight adjustment accordingly on the walkers; performing, based on a nodal surface of the wave function, crossing detection with respect to the nodal surface on the diffused walkers; and when it is not detected that any diffused walker crosses the nodal surface, performing further processing on the diffused walker, where the further processing may be performed based on a weight for the diffused walker, and may include, but not limited to, reproduction, merging, or even no processing. In some embodiments, in each iteration of the diffusion of walkers, the following operation may further be included: when a diffused walker crosses the nodal surface of the specific wave function, resetting the diffused walker to an initial setting for this iteration. In some embodiments, resetting the walker is to reset the walker to an initial setting before the start of this iteration. Furthermore, in this operation, only the walkers that cross the nodal surface of the wave function are reset, rather than all walkers.

According to embodiments of the present disclosure, a drift quantity for a walker may be expressed in an appropriate form. As an example, it may be expressed in a form corresponding to/matching the walker. Specifically, the drift quantity may be in the form of a vector whose vector dimensions match dimensions of the walker. As an example, the dimensions of the drift quantity are related to the number of electrons in the system, and are especially the product of the number of electrons and the number (3) of spatial dimensions. According to this embodiment of the present disclosure, a value of the drift quantity may be appropriately set, for example, may be initially set to an appropriate value. Preferably, the drift quantity may be set depending on the trial wave function. In some embodiments, the drift quantity may be constant across iterations, for example, the same drift quantity may be used in each iteration. In some other embodiments, the drift quantity is variable across iterations, for example, it may change according to a specific rule or a specific change function, and such a change rule or specific change function may be preset based on experience.

According to embodiments of the present disclosure, the weight for a walker may be initially preset, for example, randomly set to any initial value. In addition, the weight for the walker may be appropriately adjusted/updated when performing diffusion of the walker during each iteration. In some embodiments, the weight for the diffused walker may be adjusted based on local energy of the diffused walker. If the local energy of the diffused walker is too small, the weight may be increased, otherwise the weight may be reduced. In other words, a walker with small local energy may be "preferred". According to the present disclosure, the local energy may refer to a physical quantity defined in spatial coordinates of electrons. The local energy of the walker may be calculated using a solution known in the art, especially relying on the trial wave function, which is not described in detail here.

According to embodiments of the present disclosure, the termination condition of the iterative processing of the walkers may be any appropriate condition. In some embodiments, it can be judged whether to terminate the iteration of the diffusion of walkers based on at least one of the following conditions: the number of iterations exceeds a threshold number; and in a specific number of consecutive iterations, a change in total energy reflected by walkers is less than a specific change threshold.

In some embodiments, if the change in the total energy output is small in the specific number of consecutive iterations, for example, within a specific threshold range, the iteration may be terminated. In such a case, according to embodiments of the present disclosure, appropriate processing can be performed on the walkers during each iteration before terminating the iteration, including the above-mentioned reproduction, merging, or even no processing, and then the total energy after this iteration may be calculated to determine an energy change accordingly. In some embodiments, the total energy may be determined based on a statistical value of the energy of each walker. In an example, the total energy after this iteration can be acquired by calculating local energy of each walker and weighted averaging the local energies of the walkers. Specifically, the weighted averaging may mean weighted averaging performed based on the weights for the walkers.

In some embodiments, when the number of iterations reaches a predetermined number threshold, the iteration may be terminated. In this case, the diffusion of walkers may be performed in each iteration before terminating the iteration, and optionally, after reproduction, merging, resetting, etc. performed after the diffusion, operations to be performed for a next iteration can be specified. Specifically, to further save computing power, it is not necessary to calculate total energy in each iteration. For example, the total energy in the iteration may be calculated at each iteration or every a specific number of iterations, and then an average value of the calculated total energies may be calculated when the iteration is terminated, and alternatively, the total energy may not be calculated until the iteration terminates.

According to embodiments of the present disclosure, the trial wave function may be involved in the drift quantity, the nodal surface detection, and the local energy calculation. If the trial wave function is more accurate, the accuracy of attributes related to the ground-state energy acquired in the solution of the present disclosure is also higher, and the convergence is faster. Therefore, in the above embodiments, by constructing the accurate trial wave function by using the neural network, the accuracy of the present invention is higher and the convergence is faster.

Figure 2C:
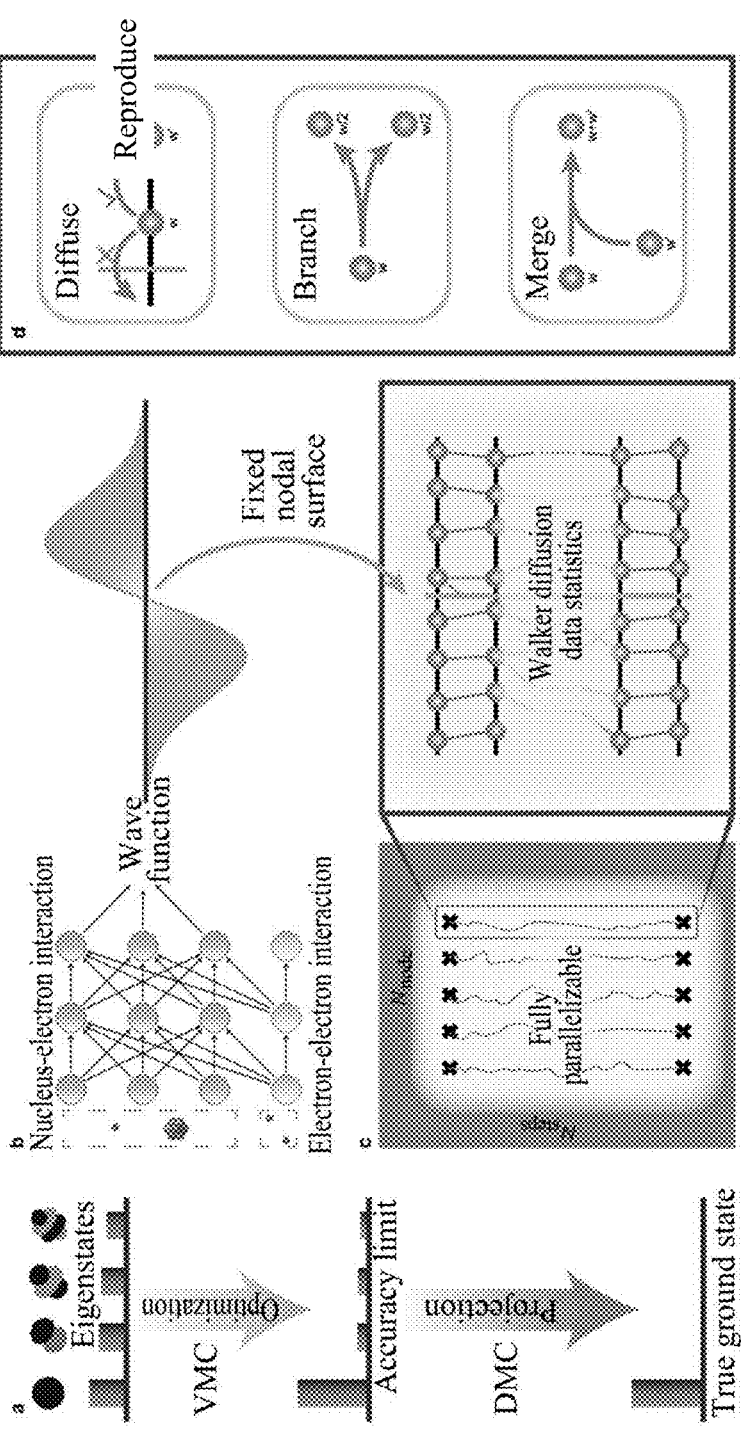
FIG. 2C shows an exemplary implementation of data processing for a quantum chemical system according to the present disclosure.

FIG. 2C shows an exemplary implementation of data processing for the quantum chemical system according to this embodiment of the present disclosure. In FIG. 2C, a indicates energy attributes of the chemical system implemented according to embodiments of the present disclosure, which may indicate proportions of components, such as a ground state and excited states in the state of the quantum chemical system, and the leftmost column indicates the proportion of the ground-state component. Compared with initial eigenstates (including ground state-energy and first to third excited-state energies from left to right), the ground-state component acquired using the variational Monte Carlo method has been improved, but the other excited-state components than the ground-state energy still exist quite obviously. In contrast, through application of the data processing method according to the present disclosure, the dominant role of the ground-state component can be further highlighted, while the other excited-state components almost disappear, which can be closer to the true ground state, so that the chemical properties of the chemical system can be more accurately acquired. In FIG. 2C, b indicates construction of a wave function, especially construction of the wave function based on a neural network, where nucleus-electron interaction and electron-electron interaction are taken into account, and the acquired wave function can achieve a fixed nodal surface for the detection in processing for walkers. The processing for walkers may be shown as c in FIG. 2C, where the walker processing includes diffusion of the walkers, and walker data statistical values of the diffused walkers may be used to simulate/acquire the chemical properties of the quantum chemical system. Specifically, the walker processing may be fully parallelized, for example, by using a plurality of computing nodes for distributed processing, which will be described in further detail below. In FIG. 2C, d indicates various exemplary operations in the diffusion of the walkers, specifically, during the diffusion operation, if a diffused walker crosses the fixed nodal surface, it will be reset, otherwise it will be subjected to appropriate processing, for example, including reproduction and merging.

According to embodiments of the present disclosure, the iterative processing for the walkers may be further optimized, thereby further improving the efficiency of the method according to the present disclosure. In embodiments of the present disclosure, the optimized processing for the walkers preferably enables the number of walkers after diffusion to remain constant, thereby facilitating more efficient data processing. Specifically, the conventional variational Monte Carlo method with limited accuracy is often used currently to obtain the trial wave function, and most of the computing software runs on CPUs correspondingly, resulting in severe limitations on accuracy and efficiency. The neural network method has strong expressive power and high computational accuracy, but the cost is a huge amount of computation, which requires GPU devices for acceleration. In view of this, the present disclosure particularly considers the comprehensive application of neural networks and GPU devices. The walker processing according to embodiments of the present disclosure can be combined with the neural network method and can be efficiently computed on the GPU devices. Therefore, the present disclosure proposes a set of methods that are easy to be combined with neural network methods, can implement efficient computations on GPU devices, and have excellent scalability, thereby fully utilizing the advantages of the neural network methods and achieving a series of high-accuracy calculation results in quantum chemistry problems.

According to embodiments of the present disclosure, the walker processing can be performed on at least one computing node, where at least one of the at least one computing node can include a graphics processing unit (GPU). According to embodiments of the present disclosure, the walker processing can be performed on a plurality of computing nodes in a distributed manner, at least one of the plurality of computing nodes includes a graphics processing unit (GPU), and a part of the walker processing is performed on each computing node. In some embodiments, the computing node may include, but not limited to, one or more processors, such as one or more CPUs, or one or more GPUs, and so on. The computing nodes may often be implemented by one or more processors that are physically integrated together. These processors are close to each other in terms of distance, and communication between them may often be considered instantaneous without consuming network communication resources. In some embodiments of the present disclosure, the walker processing enables the number of walkers after this iteration of processing to remain constant at least on the computing nodes that include the graphics processing unit (GPU). It should be noted that the "constant" here may be understood as the number of walkers remaining basically unchanged, which includes, but not limited to, the number remaining unchanged in an absolute sense, the number changing very little, etc.

According to some embodiments of the present disclosure, when the diffused walker does not cross the nodal surface of the specific wave function, specific processing is performed on the diffused walker, such that the number of walkers after this iteration of processing remains constant. In some embodiments, both reproduction and merging may be performed on the walkers. In some embodiments, the reproduction and merging of the walkers are performed in a correlated manner, which may also be referred to as being performed in pairs, substantially performed concurrently. In an example, once the reproduction is performed, the merging is performed accordingly, thereby an increase in the number of walkers caused by the reproduction may offset a reduction in the number of walkers caused by the merging, such that the total number of walkers remains unchanged. In another example, once the merging is performed, the reproduction is performed accordingly. For example, after the merging is performed, the reproduction operation is performed on an appropriate walker, for example, a walker with a maximum weight, to compensate for a reduction in the number of walkers caused by the merging, such that the total number of walkers remains unchanged. Specifically, the computing nodes are composed of GPUs. Therefore, for such processing nodes composed of GPUs, the above-mentioned reproduction and merging may be performed in a correlated manner, such that at such processing nodes composed of GPUs, the number of walkers remains unchanged in each iteration.

According to some embodiments, the walker is duplicated if the weight for the walker is greater than a specific threshold, a weight for each of two walkers obtained through duplication being half of the weight for the original walker, and at the same time, two walkers with minimum weights are selected for merging, which can ensure that the number of walkers remains unchanged. The walker processed in this way is particularly suitable for a specific processing node, especially a node containing a graphics processing unit (GPU), which may greatly improve the processing efficiency.

According to some embodiments, alternatively or additionally, if the weight for the walker is greater than the specific threshold, the walker is duplicated, the weight for each of the two walkers obtained through duplication being half of the weight for the original walker, and meanwhile, a walker that is annihilated in the merging concurrently performed is replaced with one duplicated walker. This may ensure that "reproduction" and "merging" operations can run efficiently on the specific processing node, especially the node containing the GPU, achieving compilability of modules and significantly improving efficiency.

According to embodiment of the present disclosure, the processing in the present disclosure may be performed in a distributed manner. Specifically, the processing in the present disclosure may be performed on a computing node cluster consisting of a plurality of computing nodes, and the plurality of computing nodes may communicate with each other. Therefore, performing data processing on a plurality of processing nodes in a distributed manner may further improve the efficiency and effects of data processing in the quantum chemical system. In some embodiments, the processing in the present disclosure may be distributed across a plurality of computing nodes in any appropriate manner. For example, it may be evenly distributed, and numbers of walkers may be evenly distributed; alternatively, it may be accordingly distributed according to processing capabilities of the computing nodes, and a computing node with a larger processing capability may be assigned more walkers. During the processing, the iterative processing is performed on each computing node, that is, the iteration can be performed on walkers assigned to the computing node. The processing for walkers between different computing nodes may be performed separately, and only computation results, synchronization information, etc. are communicated, thereby reducing communication overheads in distributed computing.

In some embodiments, if the processing is performed on the plurality of computing nodes, and at least one of the computing nodes is composed of GPUs, operations may be performed on the computing node composed of GPUs so that the number of walkers in the iterative processing on the computing node remains constant. As an example, for the computing node composed of GPUs, the reproduction and merging of the walkers may be performed in a correlated manner as described above, such that the total number of walkers remains unchanged. In this way, compared to current performing processing by fully using CPUs, the processing efficiency can be improved by fully using the GPUs. Preferably, the processing is entirely performed on the computing nodes composed of GPUs, thereby further improving the processing efficiency.

In embodiments of the present disclosure, distributed processing of the walkers can be performed on a plurality of computing nodes, so that a high overall parallelism of algorithm can be achieved, the communication between the computing nodes is low, and high operating efficiency can be achieved. Specifically, steps in the process that require multi-node communication mainly include: a. calculation of the total energy, which requires performing weighted averaging on local energy generated on each computing node; b. synchronization of whether to generate detection points; and c. calculation of other indicators, such as a rejection rate of walker diffusion, etc. In this way, the various processing tasks can be appropriately distributed across the computing nodes, with less communication between the computing nodes, so that the processing accuracy and efficiency can be improved while communication overheads can be reduced. In addition, the present disclosure implements horizontal expansion of the method across a computing cluster composed of a plurality of GPUs, achieving near-linear efficiency gains.

In some embodiments, to properly construct a computing node cluster, the communication latencies of the computing nodes may be extended at the beginning of the process, to ensure that the plurality of computing nodes can successfully communicate with each other and form the computing cluster.

According to embodiments of the present disclosure, the distributed computing may be performed in various appropriate manners. In some embodiments, a control node may be provided for the distributed computing. The control node is responsible for summarizing processing results from all the nodes and then notifying all the nodes of a final result. The control node may also be responsible for synchronizing the processing of all the nodes. For example, the control node may summarize local energies of walkers on each node to obtain total energy of the walkers, verify whether to terminate the iteration, and then notify each computing node of a verification result, to guide/synchronize the iterative processing of the walkers on each computing node. As an example, one of the computing nodes configured to perform distributed computing may serve as the control node. Alternatively, an additional control node may be provided, such as another server.

In some embodiments, in the distributed computing, no control node is provided. Each node may obtain information about all other nodes, then, each node may locally compute processing results of all the nodes, determine whether to continue with the iteration, and then notify all the other nodes of the determination result. Furthermore, the computing nodes may agree on a synchronization time between them.

According to some embodiments of the present disclosure, in the case of distributed processing, more robust fault tolerance mechanism and synchronization mechanism may be constructed by appropriate communication. In embodiments of the present disclosure, a detection point may be determined for each computing node for synchronization and error correction during distributed processing. Specifically, the detection point may record an intermediate state of the operation during the processing, which can be used to restore a corresponding computing state when the computing is interrupted or restarted.

In some embodiments, the detection point may be generated periodically or as required, and may be used to restore processing of the computing node when errors, interruptions, etc. occur in computing. As an example, the detection point may be generated periodically and uploaded to a remote storage cluster. If the computing is interrupted and needs to be restarted, the present invention supports automatically downloading a latest detection point from the remote storage cluster to each computing node, to implement breakpoint reconnection.

In the present disclosure, the operations of generating and uploading the detection point need to be synchronized on each computing node, and each computing node generates its own corresponding detection point and uploads it to the remote storage cluster. This process can be initiated by a computing node, whose serial numbered is zero, in the computing cluster, and upon receiving the request, the other nodes simultaneously generate and upload detection points.

There may be an extreme case where one or more computing nodes fail to successfully upload the detection points (for example, the computing process is forcefully interrupted). Therefore, in the present invention, when the detection point is used to perform breakpoint reconnection, whether the detection point downloaded by each computing node corresponds to the same time step. If not, the current computing is interrupted actively and an alarm is given accordingly, so that an operator can perform manual handling.

Therefore, the walker processing method implemented in the present disclosure can run efficiently on GPU devices, with its efficiency far exceeding that of the conventional method running on CPUs.

The method implemented in the present disclosure can utilize the neural network method as the trial wave function, achieving higher accuracy than the conventional quantum chemical method. The improved wave function is constructed, thereby improving the preprocessing accuracy, which in turn can improve the accuracy of acquiring the chemical attributes of the microscopic system of the quantum chemical system. Further, after constructing the improved wave function based on the neural network, the method implemented in the present disclosure performs operations on distributed GPUs. This allows for combination with different wave function methods based on the neural network and utilization of the parallel acceleration of GPU devices to achieve further efficiency improvements. Specifically, compared to the variational Monte Carlo method based on the neural network, the present invention can process larger chemical systems more efficiently and achieve more accurate results under the condition of using the same computing resources.

Moreover, in some sense, the improved data processing according to embodiments of the present disclosure may be considered equivalent to constructing/computing an improved wave function for characterizing the microscopic system of the quantum chemical system, such as a wave function that more accurately reflects chemical characteristics of the quantum chemical system and/or satisfies the wave function requirements of the quantum chemical system. That is, the above-mentioned data processing according to the present disclosure may be equivalent to applying information about chemical attributes of the quantum chemical system to such constructed/computed wave function, to obtain a wave function output that reflects the characteristics of the quantum chemical system and/or the wave function requirements of the quantum chemical system, thereby achieving more accurate analysis results of chemical attributes of the quantum chemical system.

FIG. 2D is a block diagram of a data processing apparatus for a quantum chemical system according to an embodiment of the present disclosure. The data processing apparatus 200A may include an acquisition unit 201 configured to acquire a specific wave function suitable for the quantum chemical system that is constructed based on a neural network; a walker processing unit 202 configured to perform walker processing based on the specific wave function, the walker processing including diffusion of walkers; and an information generation unit 203 configured to determine related information about chemical properties of the quantum chemical system based on the specific wave function and the processed walkers.

In some embodiments, the walker processing unit 202 may be configured to perform, based on a nodal surface of the specific wave function, crossing detection with respect to the nodal surface on diffused walkers, and the information generation unit 203 may be configured to determine the related information about the chemical properties of the quantum chemical system based on the specific wave function and the processed walkers when it is not detected that the diffused walker crosses the nodal surface.

In some embodiments, the walker processing unit 202 may be further configured to perform, based on a nodal surface of the specific wave function, crossing detection with respect to the nodal surface on the diffused walkers; and perform walker configuration-related processing on the diffused walkers based on a detection result of the diffused walkers, and the information generation unit 203 may be further configured to determine the related information about the chemical properties of the quantum chemical system based on the specific wave function and the processed diffused walkers.

In some embodiments, the information generation unit 203 may be further configured to adjust a walker configuration based on a weight for a diffused walker when it is not detected that the diffused walker crosses the nodal surface; and/or reset the configuration of the diffused walker when it is detected that the diffused walker crosses the nodal surface.

In some embodiments, the walker processing unit 202 may be configured to iteratively perform the diffusion of the walkers, and in each iteration of the diffusion of the walkers, perform the following operations: performing drift-diffusion on the walkers, and adjusting weights for the walkers accordingly; performing, based on the nodal surface of the specific wave function, crossing detection with respect to the nodal surface on the diffused walkers; and performing further processing on the diffused walkers when it is not detected that the diffused walkers cross the nodal surface of the specific wave function. The further processing may be performed based on the weights after diffusion, and may include, for example, reproduction, merging, or even no processing, which may be performed as described above.

In some embodiments, the walker processing unit 202 may be configured to reset the diffused walker to an initial setting for this iteration when the diffused walker crosses the nodal surface of the specific wave function.

In some embodiments, the walker processing unit 202 may be configured to, when the diffused walker does not cross the nodal surface of the specific wave function, process the diffused walker so that the number of walkers after this iteration of processing remains constant. The processing may be as described above, and will not be described in detail here.

In some embodiments, the walker processing unit 202 may be configured to perform the walker processing on at least one computing node, including but not limited to diffusion, detection, reproduction, merging, and other processing, where at least one of the at least one computing node includes a graphics processing unit (GPU). Specifically, the walker processing is performed such that after each iteration of processing, the number of walkers remains constant at least on the computing node that includes the graphics processing unit (GPU).

In some embodiments, the information generation unit 203 may be configured to: calculate local energy of each walker based on the specific wave function; perform weighted averaging on the local energy of each walker to obtain total energy reflected by all walkers; and determine, based on the total energy reflected by all the walkers, information reflecting ground-state energy of the quantum chemical system.

The processing performed by the above-mentioned units, including the diffusion of the walkers, the execution and termination of the iteration, etc., may be performed as described above, and will not be described in detail here.

It should be noted that the above-mentioned various units are merely logical modules divided according to specific functions implemented by the units, and are not used to limit specific implementations. For example, the units may be implemented by software, hardware, or a combination of software and hardware. In actual implementation, the above-mentioned various units may be implemented as separate physical entities, or may be implemented by a single entity (for example, a processor (a CPU, a DSP, etc.), or an integrated circuit). In addition, the above-mentioned various units are shown with dotted lines in the drawings to indicate that these units may not actually exist, and the operations/functions implemented by them may be implemented by a processing circuit.

In addition, although not shown, the device may further include a memory, which may store various information generated during the operations by the device and the various units included in the device, program and data used for the operations, data to be sent by a communication unit, etc. The memory may be a volatile memory and/or a non-volatile memory. For example, the memory may include, but is not limited to, a random access memory (RAM), a dynamic random access memory (DRAM), a static random access memory (SRAM), a read-only memory (ROM), and a flash memory. Certainly, the memory may alternatively be located outside of the device. Optionally, although not shown, the device may further include a communication unit, which may be used to communicate with other apparatuses. In an example, the communication unit may be implemented in an appropriate manner known in the art, for example, including communication components such as an antenna array and/or a radio frequency link, various types of interfaces, communication units, and the like. This is not described in detail here. In addition, the device may further include other components not shown, such as a radio frequency link, a baseband processing unit, a network interface, a processor, and a controller. This is not described in detail here.

The data processing for the quantum chemical system according to a second embodiment of the present disclosure will be described in detail with reference to the drawings. The second embodiment according to the present disclosure mainly aims to improve the efficiency of data processing in the quantum chemical system. In the second embodiment according to the present disclosure, improved diffusion of walkers is employed, especially a specific processing device (such as a GPU) and processing of walkers particularly suitable for such a processing device are employed, which may significantly improve the data efficiency, without being particularly limited to the determination of the trial wave function.

FIG. 3A is a flowchart of a data processing method for a quantum chemical system according to the second embodiment of the present disclosure. In the method 300, in step S301, a specific wave function suitable for the quantum chemical system is acquired; in step S302, diffusion of walkers is performed based on the specific wave function, where the diffusion is performed such that the number of walkers remains constant during processing; and in step S303, related information about chemical attributes of the quantum chemical system is determined based on the specific wave function and energy of the processed walkers.

In the second embodiment according to the present disclosure, the acquired specific wave function may be any appropriate wave function, such as a wave function used in the conventional quantum chemical method as described above, or a wave function constructed based on any appropriate neural network. According to embodiments of the present disclosure, a conventional quantum chemical method, such as a Hartree-Jastrow type wave function, may alternatively be used as a trial wave function. Specifically, a conventional wave function may be used as the trial wave function. The specific wave function here may be used for detection, energy generation, etc., for the diffused walkers as mentioned above.

In some embodiments according to the present disclosure, the walker processing, especially the diffusion, may be iteratively performed, and during each iteration, the number of diffused walkers remains substantially stable, particularly constant. Specifically, the walker processing is performed on at least one computing node, where at least one of the at least one computing node includes a graphics processing unit (GPU); and the walker processing is iteratively performed, and after each iteration of processing, the number of walkers remains constant at least on the computing node that includes the graphics processing unit (GPU).

Figure 3B:
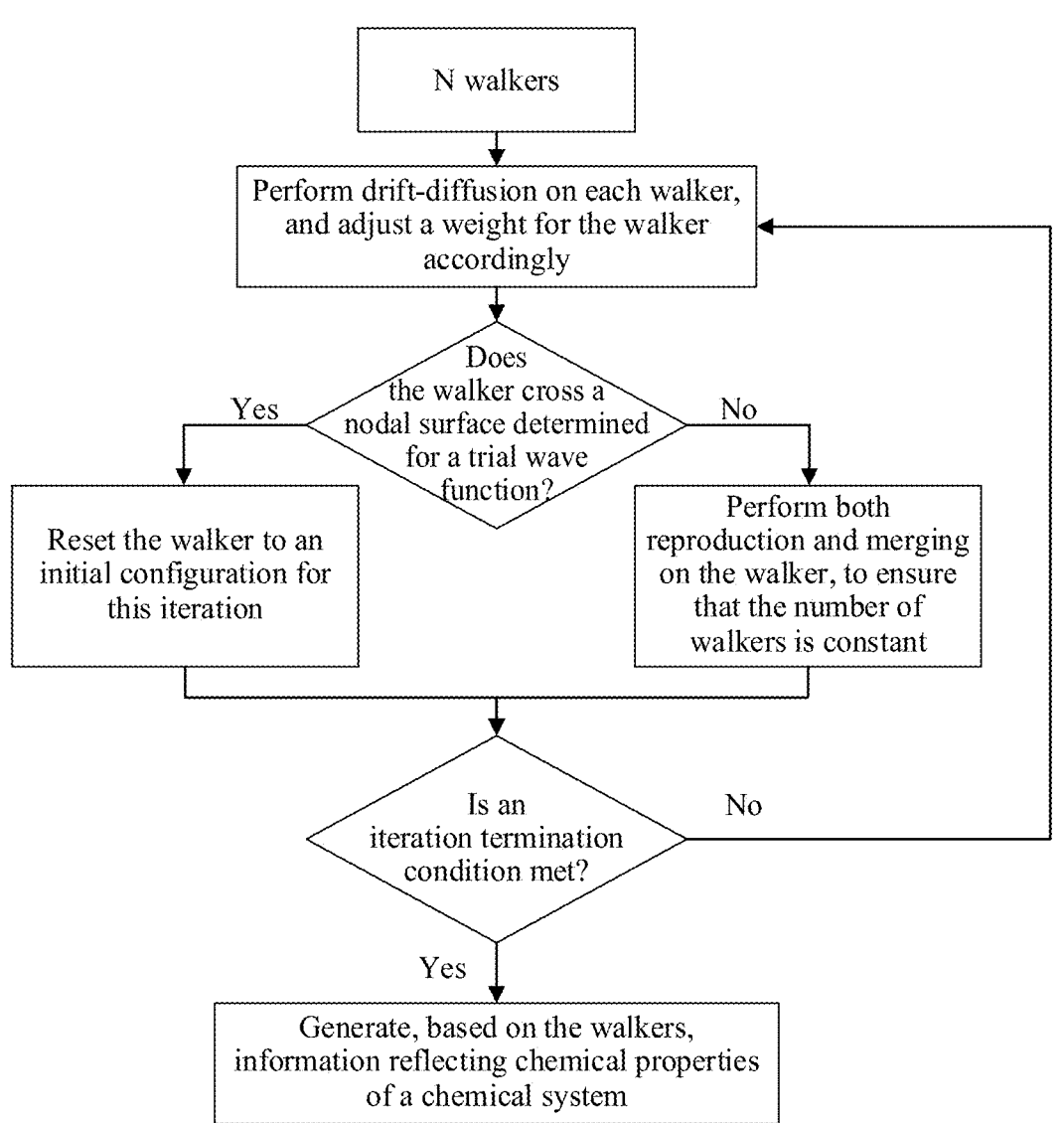
FIG. 3B shows iterative processing for walkers according to a second embodiment of the present disclosure.

FIG. 3B shows diffusion of walkers used for the quantum chemical system according to the second embodiment of the present disclosure. In iterative processing of the diffusion, likewise, a detection may also be performed based on the nodal surface of the wave function, to determine an appropriate operation for the walker. Specifically, when a diffused walker crosses an interface of the specific wave function, configuration of the walker is reset, for example, restored to an initial configuration at the beginning of this iteration, for example, an initial position. When the diffused walker does not cross a nodal surface of the specific wave function, the diffused walker is performed so that the number of walkers after this iteration of processing remains constant.

Specifically, the processing that enables the number of walkers after this iteration of processing to remain constant may include at least one of the following operations:

duplicating a walker if a weight for the walker is greater than a specific threshold, a weight for each of two walkers obtained through duplication being half of the weight for the original walker, and selecting two walkers with minimum weights for merging; and duplicating a walker if the weight for the walker is greater than the specific threshold, the weight for each of the two walkers obtained through duplication being half of the weight for the original walker, and replacing, with one duplicated walker, a walker annihilated in the merging concurrently performed.

In some embodiments of the present disclosure, the iterative processing of the walkers may be terminated according to any appropriate condition, as described above, and will not be described in detail here.

Therefore, in embodiments of the present disclosure, no matter which wave function is used as the trial wave function, the plurality of computing nodes can be effectively utilized to perform distributed data processing, thereby facilitating diffusion and achieving a high degree of parallelism. Specifically, efficient running on the GPU is achieved, thus greatly improving work efficiency.

In addition, embodiments of the present disclosure can be conveniently combined with the conventional quantum chemical method, making embodiments of the present disclosure more universal.

Figure 3C:
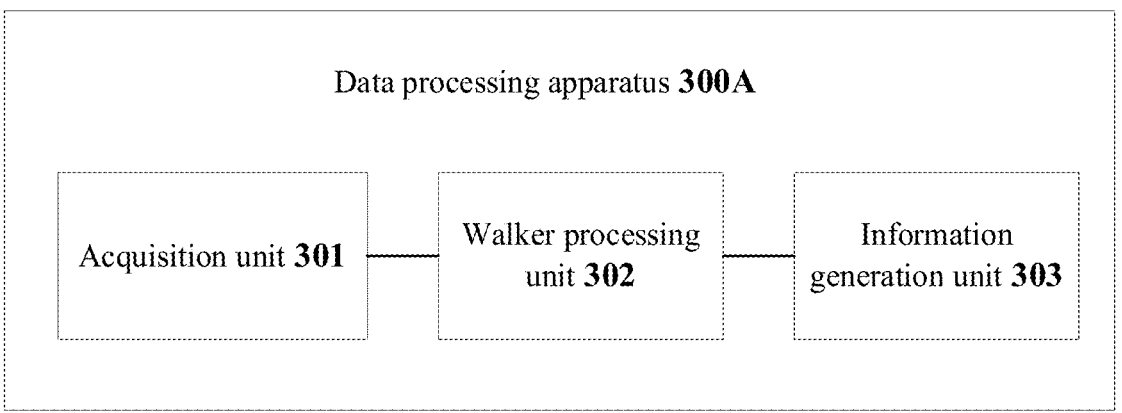
FIG. 3C is a block diagram of a data processing apparatus for a quantum chemical system according to a second embodiment of the present disclosure.

FIG. 3C is a block diagram of a data processing apparatus for a quantum chemical system according to the second embodiment of the present disclosure. The data processing apparatus 300A includes an acquisition unit 301 configured to acquire a specific wave function suitable for the quantum chemical system; a walker processing unit 302 configured to perform walker processing based on the specific wave function, the walker processing including diffusion of walkers, and the diffusion of the walkers being performed such that the number of walkers remains constant during the processing; and an information generation unit 303 configured to derive related information about chemical properties of the quantum chemical system based on the specific wave function and the processed walkers. Here, the acquisition unit, the walker processing unit, and the information generation unit may perform the above-mentioned various corresponding processing, which will not be described in detail here.

It should be noted that the above-mentioned various units are merely logical modules divided according to specific functions implemented by the units, and are not used to limit specific implementations, for example, the units may be implemented by software, hardware, or a combination of software and hardware. In actual implementation, the above-mentioned various units may be implemented as separate chemical entities, or may be implemented by a single entity (for example, a processor (a CPU, a DSP, etc.), or an integrated circuit, etc.). In addition, the above-mentioned various units are shown with dotted lines in the drawings to indicate that these units may not actually exist, and the operations/functions implemented by them may be implemented by a processing circuit. Furthermore, although not shown, the device may further include other appropriate devices, such as a memory, a communication unit, and any other suitable components, which may be as described above and will not be described in detail here.

As an example, an embodiment of the present disclosure will be verified in several classical quantum chemical systems, and compared with the results of and experimental data for mature methods in the art.

FIG. 4A to FIG. 4E show chemical attribute results obtained by the data processing solution of the quantum chemical system according to embodiments of the present disclosure. As can be seen from the drawings, the solution of the embodiment of the present disclosure can be combined with the most advanced neural network method "Fermi neural network" in current quantum chemistry, reaching a current optimal level in a series of energy calculations for the chemical systems.

Figure 4A:
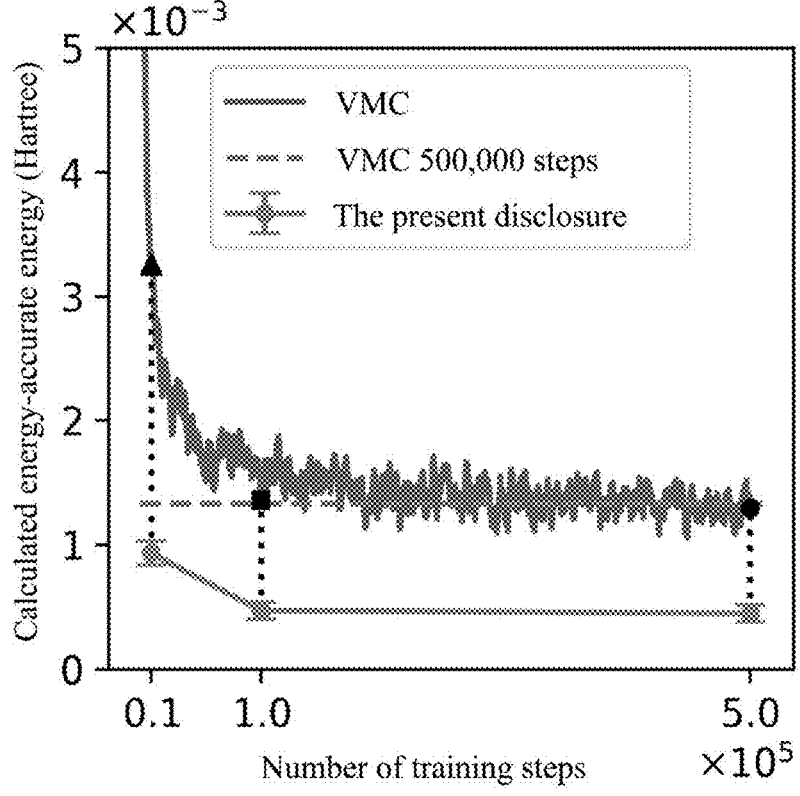
FIG. 4A to FIG. 4E show application examples of data processing for a quantum chemical system according to the present disclosure.

FIG. 4A shows energy calculation for beryllium (Be) atoms according to embodiments of the present disclosure. The present disclosure is based on the "Fermi neural network" method, but achieves a significantly higher convergence speed and accuracy than the "Fermi neural network". As can be seen from FIG. 4A, taking beryllium atoms as an example, the present invention only needs to train the "Fermi neural network" for 1,000 steps to achieve accuracy exceeding a result of training with the "Fermi neural network" alone for 50,000 steps.

Figure 4B:
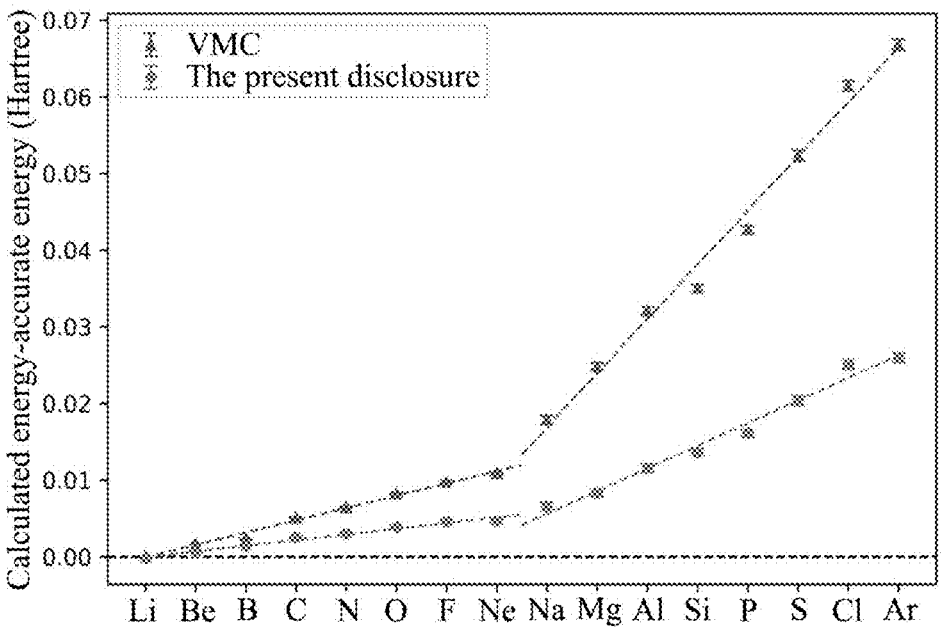

FIG. 4B shows energy calculation for a monatomic system according to embodiments of the present disclosure. To verify the effectiveness of the method in the present disclosure compared to the variational Monte Carlo method based on the neural network, a comparison is made between energy calculation results of these two methods for atoms in the second and third periods. As shown in the figure, the energy calculated in the present invention is significantly closer to true energy. It can be seen that, under a fixed amount of computing resources, the present invention can obtain more accurate results in calculations for larger systems.

Figure 4C:
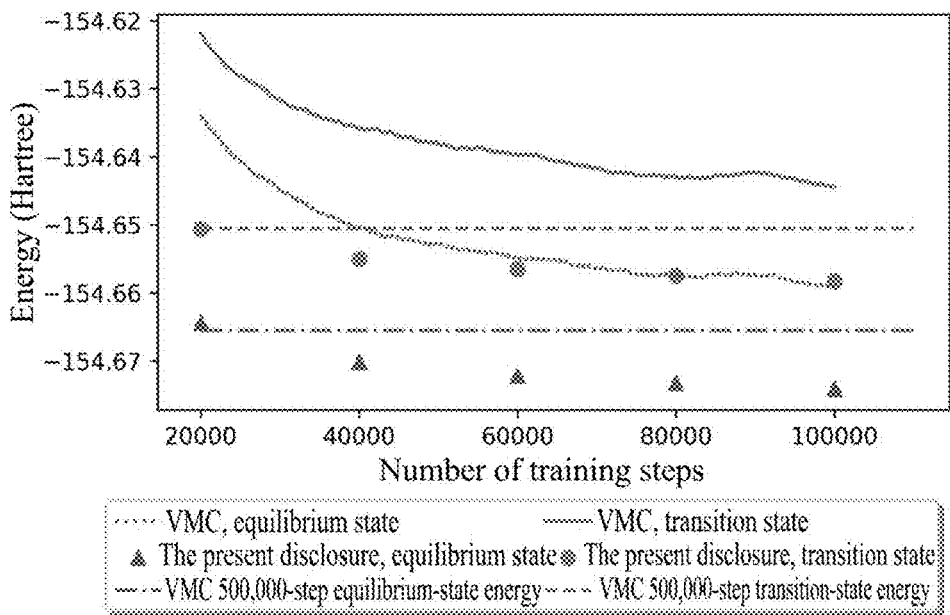
Figure 4D:
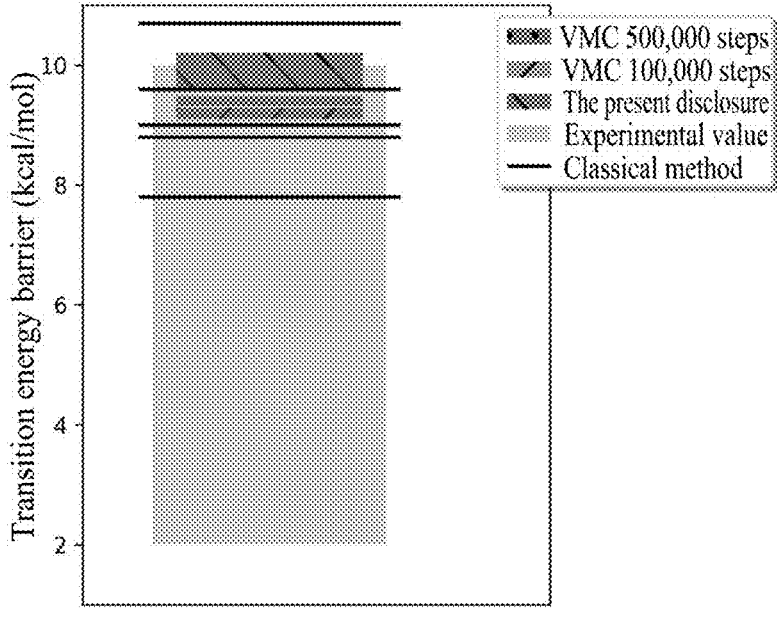

FIG. 4C shows energy calculation for cyclobutadiene according to embodiments of the present disclosure. Similarly, compared to the variational Monte Carlo using the "Fermi neural network" alone, the present invention only needs to train the "Fermi neural network" for 60,000 steps in both an equilibrium state and a transition state of cyclobutadiene to achieve more accurate energy than the variational Monte Carlo using the "Fermi neural network" alone trained for 500,000 steps. Moreover, as shown in FIG. 4D, an energy difference calculated according to the solution of the present disclosure, that is, a transition energy barrier, is also consistent with the calculation result of the variational Monte Carlo and is within the range of experimental data. It can be seen that the accuracy and efficiency of the solution of the present disclosure are also verified for cyclobutadiene molecules.

Figure 4E:
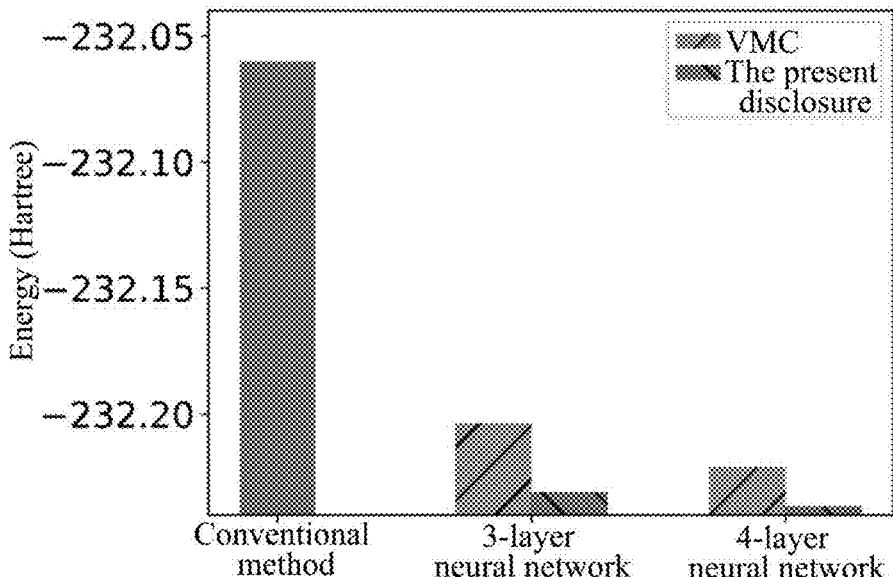

FIG. 4E shows energy calculation for a benzene ring according to embodiments of the present disclosure. The accuracy of the present invention in calculating ground-state energy of the benzene ring is obviously higher than that of the variational Monte Carlo using the "fermionic neural network" alone, and far exceeds that of the conventional method (extended to a complete basis set coupled-cluster method with single, double, and partial triple excitations). As shown in FIG. 4E, the lower the energy here, the better the corresponding method. The energy obtained by the present invention is tens of milli-Hartrees lower than that of the variational Monte Carlo using the "Fermi neural network" with the same network configuration, and is hundreds of milli-Hartrees lower than that of the conventional method.

In addition to having higher computational accuracy than the variational Monte Carlo using the "Fermi neural network" alone, the present disclosure is also higher in overall efficiency, that is, only needs to train the "Fermi neural network" for fewer steps to achieve the same or even higher accuracy.

In addition, the solution of the present disclosure has excellent scalability and may effectively utilize a cluster consisting of hundreds of NVIDIA V100 GPUs to accelerate computing, with a near-linear acceleration ratio, thereby performing high-accuracy calculation for larger chemical systems.

Figure 5:
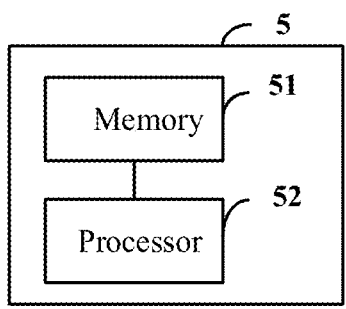
FIG. 5 is a block diagram of an electronic device according to some embodiments of the present disclosure.

Some embodiments of the present disclosure further provide an electronic device that can be operable to implement the operations/functions of the above-mentioned model pre-training device and/or model training device. FIG. 5 is a block diagram of an electronic device according to some embodiments of the present disclosure. For example, in some embodiments, the electronic device 5 may be various types of devices, for example, may include, but not limited to, mobile terminals such as a mobile phone, a notebook computer, a digital broadcast receiver, a personal digital assistant (PDA), a tablet computer (PAD), a portable multimedia player (PMP), and a vehicle-mounted terminal (such as a vehicle navigation terminal), and fixed terminals such as a digital TV and a desktop computer. For example, the electronic device 5 may include a display panel configured to display data used in the solution according to the present disclosure and/or execution results. For example, the display panel may be in various shapes, such as a rectangular panel, an elliptical panel, or a polygonal panel, etc. In addition, the display panel may be a flat panel, a curved panel, or even a spherical panel.

As shown in FIG. 5, the electronic device 5 in this embodiment includes: a memory 51 and a processor 52 coupled to the memory 51. It should be noted that the components of the electronic device 50 shown in FIG. 5 are merely exemplary and non-limiting. The electronic device 50 may further have other components according to actual application requirements. The processor 52 may control other components in the electronic device 5 to perform desired functions.

In some embodiments, the memory 51 is configured to store one or more computer-readable instructions. The processor 52 is configured to run computer-readable instructions, and the computer-readable instructions, when run by the processor 52, cause the method according to any one of the above embodiments to be implemented. For specific implementations of the steps of the method and related explanation content, reference may be made to the above embodiments, and repetitions will not be repeated here.

For example, the processor 52 and the memory 51 may communicate with each other directly or indirectly. For example, the processor 52 and the memory 51 may communicate with each other via a network. The network may include a wireless network, a wired network, and/or any combination of wireless networks and wired networks. The processor 52 and the memory 51 may also communicate with each other through a system bus, which is not limited in the present disclosure.

For example, the processor 52 may be embodied as various appropriate processors, processing apparatuses, etc., such as a central processing unit (CPU), a graphics processing unit (GPU), and a network processor (NP); or may be a digital signal processor (DSP), an application-specific integrated circuit (ASIC), a field programmable gate array (FPGA) or other programmable logic devices, a discrete gate or transistor logic device, or a discrete hardware component. The central processing unit (CPU) may be of an X86 or ARM architecture, etc. For example, the memory 51 may include any combination of various forms of computer-readable storage media, for example, a volatile memory and/or a non-volatile memory. The memory 51 may include, for example, a system memory, and the system memory stores, for example, an operating system, an application, a boot loader, a database, and other programs. Various applications and various data may also be stored in the storage medium.

Figure 6:
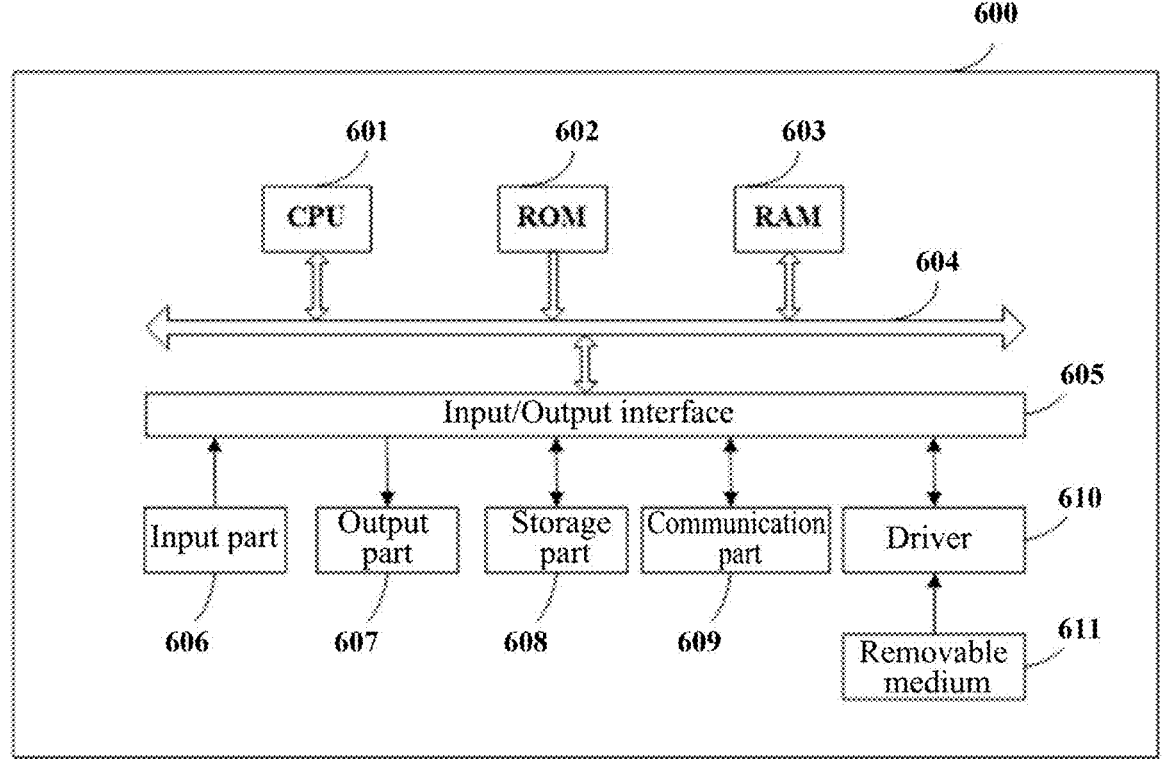
FIG. 6 is a block diagram of an electronic device according to some other embodiments of the present disclosure.

In addition, according to some embodiments of the present disclosure, when various operations/processing according to the present disclosure are implemented by software and/or firmware, programs constituting the software may be installed from the storage medium or a network to a computer system with a dedicated hardware structure, such as a computer system 600 shown in FIG. 6. When installed with various programs, the computer system can perform various functions, including the functions described above, etc. FIG. 6 is a block diagram of an example structure of a computer system that can be used according to an embodiment of the present disclosure.

In FIG. 6, a central processing unit (CPU) 601 performs various processing according to a program stored in a read-only memory (ROM) 602 or loaded from a storage part 608 into a random access memory (RAM) 603. Data required for the CPU 601 to perform various processing and the like is also stored in the RAM 603 as required. The central processing unit is merely exemplary, and it may alternatively be other types of processors, such as the various processors described above. The ROM 602, the RAM 603, and the storage part 608 may be various forms of computer-readable storage media, as described below. It should be noted that although the ROM 602, the RAM 603, and the storage device 608 are shown separately in FIG. 6, one or more of them may be combined or located in the same or different memories or storage modules.

The CPU 601, the ROM 602, and the RAM 603 are connected to one another through a bus 604. An input/output interface 605 is also connected to the bus 604.

The following components are connected to the input/output interface 605: an input part 606, for example, a touch screen, a touchpad, a keyboard, a mouse, an image sensor, a microphone, an accelerometer, or a gyroscope; an output part 607, including a display, such as a cathode-ray tube (CRT), a liquid crystal display (LCD), a speaker, or a vibrator; the storage part 608, including a hard disk, a magnetic tape, etc.; and a communication part 609, including a network interface card, such as a LAN card, or a modem. The communication part 609 allows communication processing to be performed via a network such as the Internet. It is easy to understand that although the various apparatuses or modules in the electronic device 600 shown in FIG. 6 communicate through the bus 604, they may alternatively communicate through a network or other means, where the network may include a wireless network, a wired network, and/or any combination of wireless networks and wired networks.

A driver 610 is also connected to the input/output interface 605 as required. A removable medium 611 such as a magnetic disk, an optical disk, a magneto-optical disk, or a semiconductor memory, is installed on the driver 610 as required, such that a computer program read therefrom is installed into the storage part 608 as required.

When the above-described series of processing is implemented by software, programs constituting the software may be installed from a network such as the Internet or a storage medium such as the removable medium 611.

According to an embodiment of the present disclosure, the process described above with reference to the flowcharts may be implemented as a computer software program. For example, this embodiment of the present disclosure includes a computer program product, which includes a computer program carried on a computer-readable medium, where the computer program includes program code for performing the method according to the embodiments of the present disclosure. In such an embodiment, the computer program may be downloaded from a network through the communication device 609 and installed, installed from the storage device 608, or installed from the ROM 602. When the computer program is executed by the CPU 601, the above-mentioned functions defined in the method of the embodiments of the present disclosure are performed.

It should be noted that, in the context of the present disclosure, the computer-readable medium may be a tangible medium that may contain or store a program for use by or in conjunction with an instruction execution system, apparatus, or device. The computer-readable medium may be a computer-readable signal medium, a computer-readable storage medium, or any combination thereof. The computer-readable storage medium may be, for example, but is not limited to, an electric, magnetic, optical, electromagnetic, infrared, or semi-conductive system, apparatus, or device, or any combination thereof. A more specific example of the computer-readable storage medium may include, but is not limited to: an electrical connection having one or more wires, a portable computer magnetic disk, a hard disk, a random access memory (RAM), a read-only memory (ROM), an erasable programmable read-only memory (EPROM or flash memory), an optical fiber, a portable compact disk read-only memory (CD-ROM), an optical storage device, a magnetic storage device, or any suitable combination thereof. In the present disclosure, the computer-readable storage medium may be any tangible medium containing or storing a program which may be used by or in combination with an instruction execution system, apparatus, or device. In the present disclosure, the computer-readable signal medium may include a data signal propagated in a baseband or as a part of a carrier, the data signal carrying computer-readable program code. The propagated data signal may be in various forms, including but not limited to an electromagnetic signal, an optical signal, or any suitable combination thereof. The computer-readable signal medium may also be any computer-readable medium other than the computer-readable storage medium. The computer-readable signal medium can send, propagate, or transmit a program used by or in combination with an instruction execution system, apparatus, or device. The program code contained in the computer-readable medium may be transmitted by any suitable medium, including but not limited to: electric wires, optical cables, radio frequency (RF), etc., or any suitable combination thereof.

The above computer-readable medium may be contained in the above electronic device. Alternatively, the computer-readable medium may exist independently, without being assembled into the electronic device.

In some embodiments, there is further provided a computer program. The computer program includes instructions that, when executed by a processor, cause the processor to perform the method in any one of the above embodiments. For example, the instructions may be embodied as computer program code.

In the embodiments of the present disclosure, the computer program code for performing the operations of the present disclosure may be written in one or more programming languages or a combination thereof, where the programming languages include, but are not limited to, an object-oriented programming language, such as Java, Smalltalk, and C++, and further include conventional procedural programming languages, such as "C" language or similar programming languages. The program code may be completely executed on a computer of a user, partially executed on a computer of a user, executed as an independent software package, partially executed on a computer of a user and partially executed on a remote computer, or completely executed on a remote computer or server. In the case of the remote computer, the remote computer may be connected to the computer of the user via any kind of network, including a local area network (LAN) or a wide area network (WAN), or may be connected to an external computer (for example, connected via the Internet with the aid of an Internet service provider).

The flowcharts and block diagrams in the accompanying drawings illustrate the possibly implemented architecture, functions, and operations of the system, method, and computer program product according to various embodiments of the present disclosure. In this regard, each block in the flowchart or block diagram may represent a module, program segment, or part of code, and the module, program segment, or part of code contains one or more executable instructions for implementing the specified logical functions. It should also be noted that, in some alternative implementations, the functions marked in the blocks may also occur in an order different from that marked in the accompanying drawings. For example, two blocks shown in succession can actually be performed substantially in parallel, or they can sometimes be performed in the reverse order, depending on the functions involved. It should also be noted that each block in the block diagram and/or the flowchart, and a combination of the blocks in the block diagram and/or the flowchart may be implemented by a dedicated hardware-based system that executes specified functions or operations, or may be implemented by a combination of dedicated hardware and computer instructions.

The related modules, components, or units described in the embodiments of the present disclosure may be implemented by software, or may be implemented by hardware. The names of the modules, components, or units do not constitute a limitation on the modules, components, or units themselves in some cases.

The functions described herein above may be performed at least partially by one or more hardware logic components. For example, without limitation, exemplary hardware logic components that may be used include: a field programmable gate array (FPGA), an application-specific integrated circuit (ASIC), an application-specific standard product (ASSP), a system on a chip (SOC), a complex programmable logic device (CPLD), and the like.

The present disclosure may be implemented in any form described here, including but not limited to the example embodiments enumerated below, which describe structures, features, and functions of some parts of the embodiments of the present invention.

According to some embodiments of the present disclosure, there is provided a data processing method for a quantum chemical system. The method includes: acquiring a specific wave function suitable for the quantum chemical system that is constructed based on a neural network; performing walker processing based on the specific wave function, the walker processing including diffusion of walkers; and determining related information about chemical properties of the quantum chemical system based on the specific wave function and the processed walkers.

According to some embodiments of the present disclosure, performing the walker processing based on the specific wave function further includes: performing, based on a nodal surface of the specific wave function, crossing detection with respect to the nodal surface on a diffused walker; determining the related information about the chemical properties of the quantum chemical system based on the specific wave function and the processed walker when it is not detected that the diffused walker cross the nodal surface.

According to some embodiments of the present disclosure, the walker processing based on the specific wave function is iteratively performed, and in each iteration, the following operations are performed: performing drift-diffusion on a walker, and adjusting a weight for the diffused walker accordingly; performing, based on the nodal surface of the specific wave function, crossing detection with respect to the nodal surface on the diffused walker; and performing further processing on the diffused walker when it is not detected that the diffused walkers cross the nodal surface, the further processing including processing performed based on weight for the diffused walker.

According to some embodiments of the present disclosure, the processing performed based on the weight for the diffused walker includes at least one of the following: if the weight for the diffused walker is greater than or equal to a first weight threshold, performing reproduction on the walker to duplicate the walker into two walkers; if the weight for the diffused walker is less than a second weight threshold, performing merging on the walker to merge two walkers into one walker; and if the weight for the diffused walker is greater than or equal to the second weight threshold and less than the first weight threshold, not performing reproduction and merging on the diffused walker.

According to some embodiments of the present disclosure, when the diffused walker does not cross the nodal surface of the specific wave function, a processing that enables the number of walkers after this iteration of processing to remain constant is performed on the diffused walker.

According to some embodiments of the present disclosure, the processing that enables the number of walkers after this iteration of processing to remain constant includes at least one of the following: duplicating a walker if the weight for the walker is greater than a specific threshold, a weight for each of two walkers obtained through duplication being half of the weight for the original walker, and selecting two walkers with minimum weights for merging; or duplicating a walker if the weight for the walker is greater than a specific threshold, the weight for each of the two walkers obtained through duplication being half of the weight for the original walker, and replacing, with one duplicated walker, a walker annihilated in the merging concurrently performed.

According to some embodiments of the present disclosure, the walker processing is performed on a plurality of computing nodes in a distributed manner, at least one of the plurality of computing nodes includes a graphics processing unit, and a part of the walker processing is performed on each computing node.

According to some embodiments of the present disclosure, when the walker processing is performed on a plurality of computing nodes in the distributed manner, generating a detection point synchronously among the plurality of computing nodes periodically or as required.

According to some embodiments of the present disclosure, the diffusion of walkers is iteratively performed, and the diffusion of walkers is performed such that the number of walkers after each iteration of processing remains constant at least on the computing node that includes the graphics processing unit.

According to some embodiments of the present disclosure, the related information about the chemical properties of the quantum chemical system includes a ground-state energy, and determining the related information about the chemical properties of the quantum chemical system based on the specific wave function and the processed walkers includes: calculating local energy of each walker based on the specific wave function; performing weighted averaging on the local energy of each walker to obtain total energy reflected by all walkers; and determining, based on the total energy reflected by all the walkers, information reflecting the ground-state energy of the quantum chemical system.

According to some embodiments of the present disclosure, the diffusion of walkers is iteratively performed, and the iteration of the diffusion of walkers is terminated under at least one of the following conditions: the number of iterations exceeds a threshold number; or in a specific number of consecutive iterations, a change in total energy reflected by all walkers is less than a specific change threshold.

According to some embodiments of the present disclosure, the specific wave function is a wave function that characterizes states of electrons in the quantum chemical system; and/or the specific wave function is obtained by performing training on the neural network using a variational Monte Carlo method.

According to some embodiments of the present disclosure, there is provided a data processing method for a quantum chemical system, the method includes: acquiring a specific wave function suitable for the quantum chemical system; performing walker processing based on the specific wave function, the walker processing including diffusion of walkers, and the walker processing being further performed such that the number of walkers remains constant during the processing; and determining related information about chemical properties of the quantum chemical system based on the specific wave function and the processed walkers.

According to some embodiments of the present disclosure, the walker processing is iteratively performed, and in each iteration of the walker processing, the following operations are performed: performing drift-diffusion on the walkers, and adjusting weights for the walkers accordingly; performing, based on the nodal surface of the specific wave function, crossing detection with respect to the nodal surface on the diffused walkers; and performing, on a diffused walker when it is detected that the diffused walker does not cross the nodal surface, processing that enables the number of walkers after this iteration of processing to remain constant.

According to some embodiments of the present disclosure, the processing that enables the number of walkers after this iteration of processing to remain constant includes at least one of the following: duplicating a walker if a weight for the walker is greater than a specific threshold, a weight for each of two walkers obtained through duplication being half of the weight for the original walker, and selecting two walkers with minimum weights for merging; or duplicating a walker if a weight for the walker is greater than the specific threshold, the weight for each of the two walkers obtained through duplication being half of the weight for the original walker, and replacing, with one duplicated walker, a walker annihilated in the merging concurrently performed.

According to some embodiments of the present disclosure, the walker processing is performed on the plurality of computing nodes in a distributed manner, at least one of the computing nodes includes a graphics processing unit, and a part of the walker processing is performed on each computing node, and where the walker processing is iteratively performed, and the walker processing is performed such that the number of walkers after each iteration of processing remains constant at least on the computing node that includes the graphics processing unit.

According to some embodiments of the present disclosure, there is provided a data processing apparatus for a quantum chemical system. The apparatus includes: an acquisition unit configured to acquire a specific wave function suitable for the quantum chemical system that is constructed based on a neural network; a walker processing unit configured to perform walker processing based on the specific wave function, the walker processing including diffusion of walkers; and an information generation unit configured to determine related information about chemical properties of the quantum chemical system based on the specific wave function and the processed walkers.

According to some embodiments of the present disclosure, there is provided a data processing apparatus for a quantum chemical system. The apparatus includes: an acquisition unit configured to acquire a specific wave function suitable for the quantum chemical system; a walker processing unit configured to performs walker processing based on the specific wave function, the walker processing including diffusion of walkers, and the walker processing being further performed such that the number of walkers remains constant during the processing; and an information generation unit configured to determine related information about chemical properties of the quantum chemical system based on the specific wave function and the processed walkers.

According to still some embodiments of the present disclosure, there is provided an electronic device. The electronic device includes: a memory; and a processor coupled to the memory, where the memory stores instructions that, when executed by the processor, cause the electronic device to perform the method according to any one of the embodiments of the present disclosure.

According to still some embodiments of the present disclosure, there is provided a computer-readable storage medium having a computer program stored thereon, where the program, when executed by a processor, causes the method according to any one of the embodiments of the present disclosure to be implemented.

According to still some embodiments of the present disclosure, there is provided a computer program. The computer program includes: instructions that, when executed by a processor, cause the processor to perform the method according to any one of the embodiments of the present disclosure.

According to some embodiments of the present disclosure, there is provided a computer program product including instructions that, when executed by a processor, cause the method according to any one of the embodiments of the present disclosure to be implemented.

The foregoing descriptions are merely some embodiments of the present disclosure and explanations of the applied technical principles. Those skilled in the art should understand that the scope of disclosure involved in the present disclosure is not limited to the technical solutions formed by specific combinations of the foregoing technical features, and shall also cover other technical solutions formed by any combination of the foregoing technical features or equivalent features thereof without departing from the foregoing concept of disclosure. For example, a technical solution formed by a replacement of the foregoing features with technical features with similar functions disclosed in the present disclosure (but not limited thereto) also falls within the scope of the present disclosure.

In the description provided herein, numerous specific details are set forth. However, it is understood that the embodiments of the present invention may be practiced without these specific details. In other cases, well-known methods, structures, and techniques have not been shown in detail in order not to obscure the understanding of this description.

In addition, although the various operations are depicted in a specific order, it should be understood as requiring these operations to be performed in the specific order shown or in a sequential order. Under certain circumstances, multitasking and parallel processing may be advantageous. Similarly, although several specific implementation details are included in the foregoing discussions, these details should not be construed as limiting the scope of the present disclosure. Some features that are described in the context of separate embodiments can also be implemented in combination in a single embodiment. In contrast, various features described in the context of a single embodiment may alternatively be implemented in a plurality of embodiments individually or in any suitable subcombination.

While some specific embodiments of the present disclosure have been exemplarily described in detail, it should be understood by those skilled in the art that the above examples are merely for illustration and are not intended to limit the scope of the present disclosure. Those skilled in the art should understand that various modifications can be made to the above embodiments, without departing from the scope and spirit of the present disclosure. The scope of the present disclosure is defined by the appended claims.

The invention claimed is:

1. A data processing method for a quantum chemical system, the method comprising, by at least one computing node comprising a graphics processing unit:
   constructing a specific wave function suitable for the quantum chemical system based on a neural network, wherein the specific wave function is a wave function that characterizes states of electrons in the quantum chemical system, wherein constructing the specific wave function suitable for the quantum chemical system based on the neural network comprises: training the neural network by using a variational Monte Carlo method with an initial electron distribution configuration as an input and with minimizing an energy state as a training goal, wherein corresponding network parameters when the energy reaches a minimum value correspond to the specific wave function;

performing walker processing on walkers based on the specific wave function, wherein a walker corresponds to an electron in the quantum chemical system and comprises information about electron attributes in the quantum chemical system; and determining relevant information of chemical properties of the quantum chemical system based on the specific wave function and the processed walkers, the relevant information of the chemical properties of the quantum chemical system comprises attributes related to ground-state energy of electrons in the quantum chemical system, wherein performing the walker processing on the walkers based on the specific wave function is executed iteratively, and in each iteration, performing the walker processing further comprises:
   performing drift-diffusion on a walker with a preset drift amount;
   adjusting a weight for a diffused walker based on a local energy of the diffused walker;
   detecting whether the diffused walker crosses a nodal surface of the specific wave function, by judging whether a spatial position of the diffused walker crosses the nodal surface, wherein the nodal surface of the specific wave function is a plane comprised of all of points of the specific wave function having a value of zero; and
   performing processing related to a walker configuration on diffused walkers based on a detection result of the diffused walkers, wherein performing the processing related to the walker configuration on the diffused walkers based on the detection result of the diffused walkers, further comprises: in response to detecting that the diffused walker does not cross the nodal surface of the specific wave function, performing further processing based on the weight for the diffused walker, wherein the further processing comprises at least one of reproduction, merging, or no operation on the diffused walker, and wherein determining the relevant information of the chemical properties of the quantum chemical system based on the specific wave function and the processed walkers further comprises:
   calculating statistical data of the processed walkers based on the specific wave function, to determine the relevant information of the chemical properties of the quantum chemical system, wherein the statistical data comprises statistical data of energies of the walkers.

2. The method of claim 1, wherein performing the processing related to the walker configuration on the diffused walkers based on the detection result of the diffused walkers further comprises:
   resetting a configuration of a diffused walker when it is detected that the diffused walker crosses the nodal surface.

3. The method of claim 1, wherein performing the further processing based on the weight for the diffused walker comprises at least one of the following:
   in response to the weight for the diffused walker being greater than or equal to a first weight threshold, performing reproduction on the diffused walker to duplicate the diffused walker into two walkers;
   in response to the weight for the diffused walker being less than a second weight threshold, performing merging on the diffused walker to merge two walkers into one walker; or in response to the weight for the diffused walker being greater than or equal to the second weight threshold and less than the first weight threshold, not performing the reproduction and merging on the diffused walker.

4. The method of claim 1, wherein performing processing related to the walker configuration on the diffused walkers based on the detection result of the diffused walkers, further comprises:

in response to detecting that the diffused walker does not cross the nodal surface of the specific wave function, performing a processing on the diffused walker that enables a number of walkers after this iteration of processing to remain constant.

5. The method of claim 4, wherein the processing that enables the number of walkers after this iteration of processing to remain constant comprises at least one of the following:

duplicating an original walker if a weight for the original walker is greater than a specific threshold, a weight for each of two walkers obtained through the duplication being half of the weight for the original walker, and selecting two walkers with minimum weights for merging; or duplicating the original walker if the weight for the original walker is greater than a specific threshold, the weight for each of the two walkers obtained through the duplication being half of the weight for the original walker, and replacing, with one duplicated walker, a walker annihilated in the merging concurrently performed.

6. The method of claim 1, wherein the walker processing is performed on a plurality of computing nodes in a distributed manner, at least one of the plurality of computing nodes comprises a graphics processing unit, and a part of the walker processing is performed on each computing node, and wherein the drift-diffusion of walkers is iteratively performed, and the drift-diffusion of walkers is performed such that after each iteration of processing, a number of walkers remain constant at least on the computing node that comprises the graphics processing unit.

7. The method of claim 1, wherein when the walker processing is performed on a plurality of computing nodes in a distributed manner, a detection point is generated synchronously among the plurality of computing nodes periodically or as required, and wherein the drift-diffusion of walkers is iteratively performed, and the drift-diffusion of walkers is performed such that after each iteration of processing, a number of walkers remain constant at least on the computing node that comprises the graphics processing unit.

8. The method of claim 1, wherein determining the relevant information of the chemical properties of the quantum chemical system based on the specific wave function and the processed walkers comprises:

calculating local energy of each walker based on the specific wave function;

performing weighted averaging on the local energy of each walker to obtain total energy reflected by all walkers; and determining, based on the total energy reflected by all the walkers, information reflecting the ground-state energy of the quantum chemical system.

9. The method of claim 8, wherein the drift-diffusion of walkers is iteratively performed, and the iteration of the drift-diffusion of walkers is terminated under at least one of the following conditions:

a number of iterations exceeds a threshold number; or in a specific number of consecutive iterations, a change in the total energy reflected by all the walkers is less than a specific change threshold.

10. An electronic device, comprising:

a memory; and a processor coupled to the memory, wherein the memory stores executable instructions that, when executed by the processor, cause the electronic device to perform:

constructing a specific wave function suitable for a quantum chemical system based on a neural network, wherein the specific wave function is a wave function that characterizes states of electrons in the quantum chemical system, wherein constructing the specific wave function suitable for the quantum chemical system based on the neural network comprises: training the neural network by using a variational Monte Carlo method with an initial electron distribution configuration as an input and with minimizing an energy state as a training goal, wherein corresponding network parameters when the energy reaches a minimum value correspond to the specific wave function;

performing walker processing on walkers based on the specific wave function, wherein a walker corresponds to an electron in the quantum chemical system and comprises information about electron attributes in the quantum chemical system; and determining relevant information of chemical properties of the quantum chemical system based on the specific wave function and the processed walkers, the relevant information of the chemical properties of the quantum chemical system comprises attributes related to ground-state energy of electrons in the quantum chemical system, wherein performing the walker processing on the walkers based on the specific wave function is executed iteratively, and in each iteration, performing the walker processing further comprises:

performing drift-diffusion on a walker with a preset drift amount;

adjusting a weight for a diffused walker based on a local energy of the diffused walker;

detecting whether the diffused walker crosses a nodal surface of the specific wave function, by judging whether a spatial position of the diffused walker crosses the nodal surface, wherein the nodal surface of the specific wave function is a plane comprised of all of points of the specific wave function having a value of zero; and performing processing related to a walker configuration on diffused walkers based on a detection result of the diffused walkers, wherein performing the processing related to the walker configuration on the diffused walkers based on the detection result of the diffused walkers, further comprises: in response to detecting that the diffused walker does not cross the nodal surface of the specific wave function, performing further processing based on the weight for the diffused walker, wherein the further processing comprises at least one of reproduction, merging, or no operation on the diffused walker, and wherein determining the relevant information of the chemical properties of the quantum chemical system based on the specific wave function and the processed walkers further comprises:

calculating statistical data of the processed diffused walkers based on the specific wave function, to determine the relevant information of the chemical properties of the quantum chemical system, wherein the statistical data comprises statistical data of energies of the walkers.

11. The electronic device of claim 10, wherein performing the further processing based on the weight for the diffused walker comprises at least one of the following:

in response to the weight for the diffused walker being greater than or equal to a first weight threshold, performing reproduction on the diffused walker to duplicate the diffused walker into two walkers;

in response to the weight for the diffused walker being less than a second weight threshold, performing merging on the diffused walker to merge two walkers into one walker; or in response to the weight for the diffused walker being greater than or equal to the second weight threshold and less than the first weight threshold, not performing the reproduction and merging on the diffused walker.

12. The electronic device of claim 10, wherein performing the processing related to the walker configuration on the diffused walkers based on the detection result of the diffused walkers further comprises:

resetting a configuration of a diffused walker when it is detected that the diffused walker crosses the nodal surface.

13. The electronic device of claim 10, wherein performing the processing related to the walker configuration on the diffused walkers based on the detection result of the diffused walkers, further comprises:

in response detecting that the diffused walker does not cross the nodal surface of the specific wave function, performing a processing on the diffused walker that enables a number of walkers after this iteration of processing to remain constant.

14. The electronic device of claim 13, wherein the processing that enables the number of walkers after this iteration of processing to remain constant comprises at least one of the following:

duplicating an original walker if a weight for the original walker is greater than a specific threshold, a weight for each of two walkers obtained through the duplication being half of the weight for the original walker, and selecting two walkers with minimum weights for merging; or duplicating the original walker if the weight for the original walker is greater than a specific threshold, the weight for each of the two walkers obtained through the duplication being half of the weight for the original walker, and replacing, with one duplicated walker, a walker annihilated in the merging concurrently performed.

15. The electronic device of claim 10, wherein determining the relevant information of the chemical properties of the quantum chemical system based on the specific wave function and the processed walkers comprises:

calculating local energy of each walker based on the specific wave function;

performing weighted averaging on the local energy of each walker to obtain total energy reflected by all walkers; and determining, based on the total energy reflected by all the walkers, information reflecting the ground-state energy of the quantum chemical system.

16. A non-transitory computer-readable storage medium having executable instructions stored thereon, wherein the instructions, when executed by a processor, cause implementation of:

constructing a specific wave function suitable for a quantum chemical system based on a neural network, wherein the specific wave function is a wave function that characterizes states of electrons in the quantum chemical system, wherein constructing the specific wave function suitable for the quantum chemical system based on the neural network comprises: training the neural network by using a variational Monte Carlo method with an initial electron distribution configuration as an input and with minimizing an energy state as a training goal, wherein corresponding network parameters when the energy reaches a minimum value correspond to the specific wave function;

performing walker processing on walkers based on the specific wave function, wherein a walker corresponds to an electron in the quantum chemical system and comprises information about electron attributes in the quantum chemical system; and determining relevant information of chemical properties of the quantum chemical system based on the specific wave function and the processed walkers, the relevant information of the chemical properties of the quantum chemical system comprises attributes related to ground-state energy of electrons in the quantum chemical system, wherein performing the walker processing on the walkers based on the specific wave function is executed iteratively, and in each iteration, performing the walker processing further comprises:

performing drift-diffusion on a walker with a preset drift amount;

adjusting a weight for a diffused walker based on a local energy of the diffused walker;

detecting whether the diffused walker crosses a nodal surface of the specific wave function, by judging whether a spatial position of the diffused walker crosses the nodal surface, wherein the nodal surface of the specific wave function is a plane comprised of all of points of the specific wave function having a value of zero; and performing processing related to a walker configuration on diffused walkers based on a detection result of the diffused walkers, wherein performing the processing related to the walker configuration on the diffused walkers based on the detection result of the diffused walkers, further comprises: in response to detecting that the diffused walker does not cross the nodal surface of the specific wave function, performing further processing based on the weight for the diffused walker, wherein the further processing comprises at least one of reproduction, merging, or no operation on the diffused walker, and wherein determining the relevant information of the chemical properties of the quantum chemical system based on the specific wave function and the processed walkers further comprises:

calculating statistical data of the processed diffused walkers based on the specific wave function, to determine the relevant information of the chemical properties of the quantum chemical system, wherein the statistical data comprises statistical data of energies of the walkers.

17. The non-transitory computer-readable storage medium of claim 16, wherein performing the further processing performed based on the weight for the diffused walker comprises at least one of the following:

in response to the weight for the diffused walker being greater than or equal to a first weight threshold, performing reproduction on the diffused walker to duplicate the diffused walker into two walkers;

in response to the weight for the diffused walker being less than a second weight threshold, performing merging on the diffused walker to merge two walkers into one walker; or in response to the weight for the diffused walker being greater than or equal to the second weight threshold and less than the first weight threshold, not performing the reproduction and merging on the diffused walker.

18. The non-transitory computer-readable storage medium of claim 16, wherein performing the processing related to the walker configuration on the diffused walkers based on the detection result of the diffused walkers further comprises:

resetting a configuration of a diffused walker when it is detected that the diffused walker crosses the nodal surface.

19. The non-transitory computer-readable storage medium of claim 16, wherein performing the processing related to the walker configuration on the diffused walkers based on the detection result of the diffused walkers, further comprises:

in response to detecting that the diffused walker does not cross the nodal surface of the specific wave function, performing a processing on the diffused walker that enables a number of walkers after this iteration of processing to remain constant.

20. The non-transitory computer-readable storage medium of claim 19, wherein the processing that enables the number of walkers after this iteration of processing to remain constant comprises at least one of the following:

duplicating an original walker if a weight for the original walker is greater than a specific threshold, a weight for each of two walkers obtained through the duplication being half of the weight for the original walker, and selecting two walkers with minimum weights for merging; or duplicating the original walker if the weight for the original walker is greater than a specific threshold, the weight for each of the two walkers obtained through the duplication being half of the weight for the original walker, and replacing, with one duplicated walker, a walker annihilated in the merging concurrently performed.

* * * * *